(12) United States Patent
Soper et al.

(10) Patent No.: US 7,901,348 B2
(45) Date of Patent: Mar. 8, 2011

(54) CATHETERSCOPE 3D GUIDANCE AND INTERFACE SYSTEM

(75) Inventors: Timothy D. Soper, Seattle, WA (US); Robb W. Glenny, Bellevue, WA (US); Eric J. Seibel, Seattle, WA (US)

(73) Assignee: University of Washington, Seattle, WA (US)

( * ) Notice: Subject to any disclaimer, the term of this patent is extended or adjusted under 35 U.S.C. 154(b) by 602 days.

(21) Appl. No.: 11/009,699

(22) Filed: Dec. 10, 2004

(65) Prior Publication Data

US 2005/0182295 A1    Aug. 18, 2005

Related U.S. Application Data

(60) Provisional application No. 60/529,077, filed on Dec. 12, 2003.

(51) Int. Cl.
*A61B 1/00* (2006.01)
*A61B 1/04* (2006.01)

(52) U.S. Cl. .......................... 600/117; 600/139

(58) Field of Classification Search .................. 600/103, 600/117, 118, 411
See application file for complete search history.

(56) References Cited

U.S. PATENT DOCUMENTS

| | | | |
|---|---|---|---|
| 4,695,163 A | 9/1987 | Schachar | 356/369 |
| 5,765,561 A * | 6/1998 | Chen et al. | 600/407 |
| 6,148,095 A | 11/2000 | Prause et al. | 382/131 |
| 6,241,657 B1 * | 6/2001 | Chen et al. | 600/117 |
| 6,443,894 B1 * | 9/2002 | Sumanaweera et al. | 600/443 |
| 6,466,687 B1 | 10/2002 | Uppaluri et al. | 382/128 |
| 6,546,271 B1 | 4/2003 | Reisfeld | 600/407 |
| 6,773,394 B2 * | 8/2004 | Taniguchi et al. | 600/117 |
| 6,785,571 B2 | 8/2004 | Glossop | 600/424 |

(Continued)

FOREIGN PATENT DOCUMENTS

EP    0 713 672    5/1996

(Continued)

OTHER PUBLICATIONS

Solomon et al. 2000 "Three-dimensional CT-Guided Bronchoscopy With a Real-Time Electromagnetic Position Sensor," "A Comparison of Two Image Registration Methods." *The Departments of Cardiovascular and Interventional Radiology* (Dr. Solomon) *and Pulmonary Medicine* (Drs. White, Wiener, Orens, and Wang) *John Hopkins School of Medicine*. 5pp. 1783-1787.

(Continued)

*Primary Examiner* — Thomas J Sweet
*Assistant Examiner* — Philip R Smith
(74) *Attorney, Agent, or Firm* — Ronald M. Anderson

(57) ABSTRACT

Visual-assisted guidance of an ultra-thin flexible endoscope to a predetermined region of interest within a lung during a bronchoscopy procedure. The region may be an opacity-identified by non-invasive imaging methods, such as high-resolution computed tomography (HRCT) or as a malignant lung mass that was diagnosed in a previous examination. An embedded position sensor on the flexible endoscope indicates the position of the distal tip of the probe in a Cartesian coordinate system during the procedure. A visual display is continually updated, showing the present position and orientation of the marker in a 3-D graphical airway model generated from image reconstruction. The visual display also includes windows depicting a virtual fly-through perspective and real-time video images acquired at the head of the endoscope, which can be stored as data, with an audio or textual account.

48 Claims, 15 Drawing Sheets

U.S. PATENT DOCUMENTS

| | | | | |
|---|---|---|---|---|
| 6,788,967 | B2 * | 9/2004 | Ben-Haim et al. | 600/424 |
| 6,892,090 | B2 * | 5/2005 | Verard et al. | 600/424 |
| 2001/0055462 | A1 * | 12/2001 | Seibel | 385/147 |
| 2002/0087101 | A1 | 7/2002 | Barrick et al. | 600/587 |
| 2002/0133057 | A1 * | 9/2002 | Kukuk | 600/101 |
| 2003/0032878 | A1 | 2/2003 | Shahidi | 600/429 |
| 2003/0045778 | A1 * | 3/2003 | Ohline et al. | 600/114 |
| 2003/0103665 | A1 | 6/2003 | Uppaluri et al. | 382/131 |
| 2003/0160721 | A1 | 8/2003 | Gilboa et al. | 342/450 |
| 2004/0015053 | A1 | 1/2004 | Bieger et al. | 600/117 |
| 2004/0249267 | A1 | 12/2004 | Gilboa | 600/204 |
| 2005/0020878 | A1 * | 1/2005 | Ohnishi et al. | 600/117 |
| 2005/0065433 | A1 * | 3/2005 | Anderson | 600/424 |

FOREIGN PATENT DOCUMENTS

| | | |
|---|---|---|
| EP | 0 520 388 | 9/1996 |
| EP | 1 077 360 A1 | 2/2001 |
| EP | 1 088 515 A1 | 4/2001 |
| EP | 0 712 032 | 12/2001 |
| EP | 1 421 913 A1 | 10/2003 |
| WO | WO 01/97902 | 12/2001 |

OTHER PUBLICATIONS

Shinagawam, Naofumi et al. 2003 "CT-Guided Transbronchial Biopsy Using an Ultrathin Bronchoscopic Navigation." *The First Department of Medicine, Department of Radiology, School of Medicine, and the Department of Medical Oncology, Graduate School of Medicine, Hokkaido University*, Sapporo Japan 6pp. 1138-1143.

Schwartz, Yehuda et al. 2003 "Electromagnetic Navigation during Flexible Bronchoscopy." *Interventional Pulmonology, Respiration* 7pp, 770:516-522.

Mori, Kensaku et al. 2000 "A Method for Tracking camera motion of real endoscope by using virtual endoscopy system." <www.http://www.toriwaki.nuie.nagoya-u.ac.jp> 12pp. 1-12.

Kiraly, A.P. et al 2004 "Three-Dimensional Path Planning for Virtual Bronchoscopy." *IEEE Transactions on Medical Imaging*, vol. 23, No. 9, Sep. 2004. 15pp. 1365-1379.

Shoji et al. 2001 "Camera motion tracking of real endoscope by using virtual endoscopy system and texture information." *Medical Imaging 2001: Physiology and Function from Multidimensional Images*, Chin-Tu Chen, Anne V. Clough, Editors, *Proceedings of SPIE* vol. 4321 (2001) © 2001 SPIE—1605 7422/01 12pp. 122-133.

Xu et al. 2004 "3D Motion Tracking of pulmonary lesions using CT fluoroscopy images for robotically assisted lung biopsy."*Medical Imaging 2004: Visualization, Image-Guided Procedures, and Display*, edited by Robert L. Galloway, Jr., *Proceedings of SPIE* vol. 5367(*SPIE*, Bellingham, WA, 2004) 1605-/7422/04. 9pp. 394-402.

Higgins et al. 2003 "Integrated Bronchoscopic Video Tracking and 3D CT Registration for Virtual Bronchoscopy." *Medical Imaging 2003: Physiology and function: Methods, Systems, and Applications*, Anne V. Clough, Amir A. Amini, Editors, *Proceedings of SPIE* vol. 5031 (2003) © 2003 SPIE. 10pp. 80-89.

Pagoulatos et al. 2000yu "Image-based Registration of Ultrasound and Magnetic Resonance Images: A Preliminary Study." *In Medical imaging 2000: Image Display and Visualization*, Seong K. Mun, Editor, *Proceedings of SPIE* vol. 3976 (2000) 1605-7422/00. 9pp. 156-164.

Deschamps et al. © 1999 "Automatic construction of minimal paths in 3D images: An application to virtual endoscopy." *CARS'99*—H.U. Lemke, M.W. Vannier, K. Inamura & A.G. Fannan (Editors) © 1999 Elsevier Science B.V. All rights reserved. 5pp. 151-155.

Shahidi et al. 2002 "Implementation, Calibration and Accuracy Testing of an Image-Enhanced Endoscopy System." *IEEE Transactions on Medical Imaging* vol. 21, No. 12, Dec. 2002. 12pp. 1524-1535.

Herline et al. 1999 "Surface Registration for Use in Interactive, Image-Guided Liver Surgery." *Presented at the Second International Conference on Medical Image Computing and Computer-Assisted Intervention (MICCAI'99)*, Cambridge, England, Sep. 1999. 7pp 5:11-17.

Oikawa et al. 2003 "Intra-operative Guidance with Real-time Information of Open MRI and Manipulators Using Coordinate-Integration Module." *Visualization, Image-Guided Procedures, and Display*, Robert L. Galloway Jr., Editor, *Proceedings of SPIE* vol. 5029 (2003) © 2003 *SPIE* 1605-7422/03. 8pp. 653-660.

Yu et al. 2001 "3D Navigation for Endoscope by Magnetic Field." *Data Mining and Applications.* Deren Li, Jie Yang, Jufu Feng, Shen Wei, Editors, *Proceedings of SPIE* vol. 4556 (2001) *SPIE*—0277-786X/01. 4pp. 25-28.

* cited by examiner

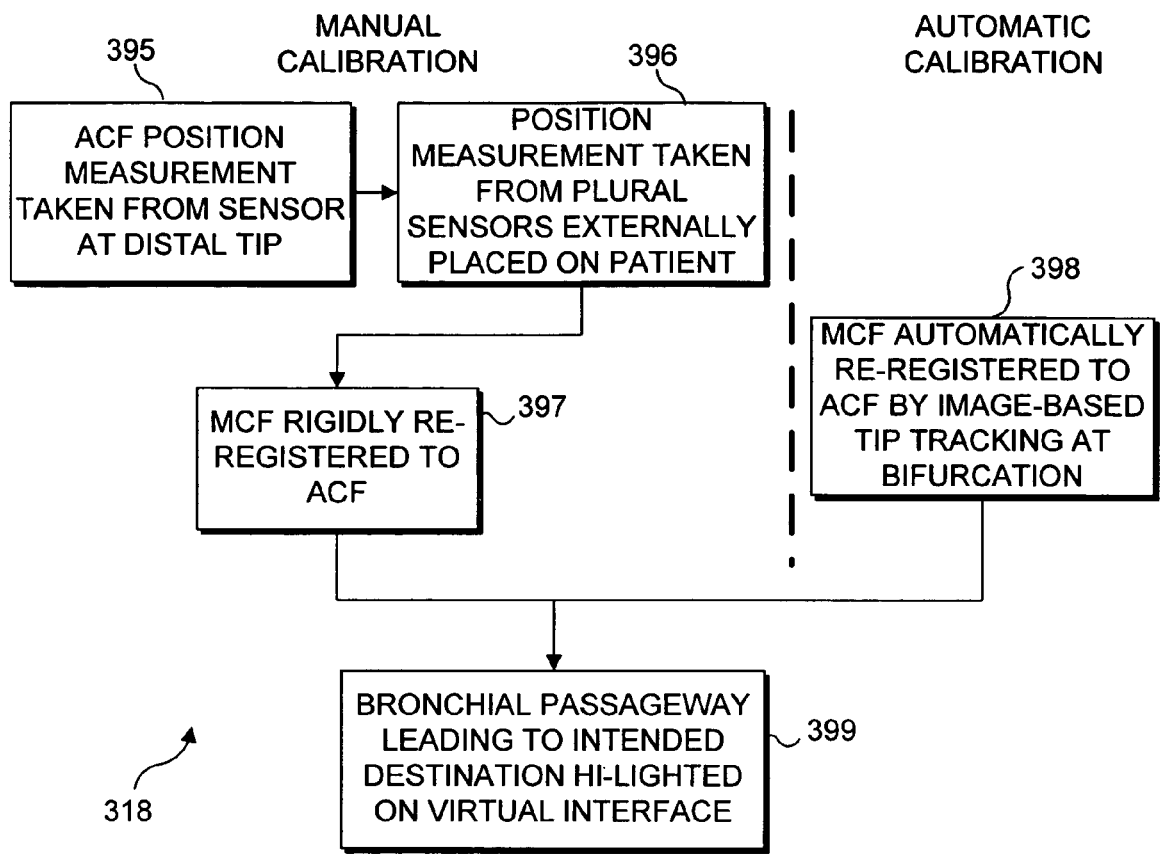
*FIG. 8F*
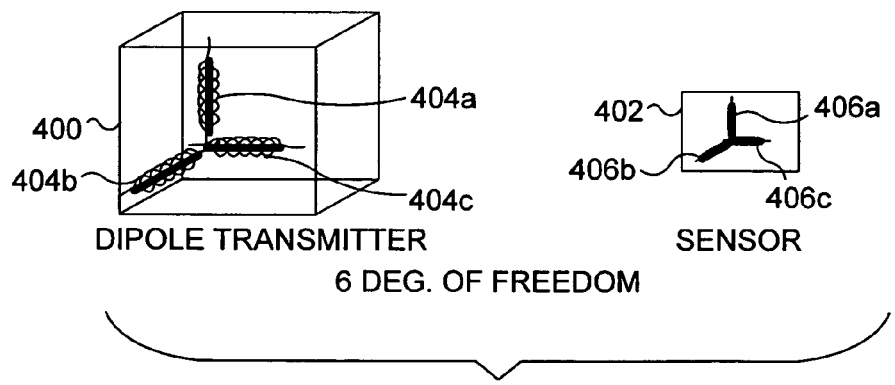
*FIG. 9A*
*FIG. 9B*          *FIG. 9C*

CATHETERSCOPE 3D GUIDANCE AND INTERFACE SYSTEM

RELATED APPLICATIONS

This application is based on a prior copending provisional application, Ser. No. 60/529,077, filed on Dec. 12, 2003, the benefit of the filing date of which is hereby claimed under 35 U.S.C. §119(e).

FIELD OF THE INVENTION

This invention generally relates to a method and apparatus for providing three-dimensional (3-D) guidance to a catheterscope or flexible endoscope that is being advanced through a branching lumen in a patient's body, and more specifically, to the use of a 3-D model in connection with a sensor, for determining the disposition and orientation of a flexible endoscope, for visually guiding the flexible endoscope through a series of branching lumens in a patient's body.

BACKGROUND OF THE INVENTION

On high-resolution computed tomography (HRCT) scans, potentially cancerous masses appear as radio-opaque nodules. "Screening" HRCT scans are now offered commercially to target patients at high risk for lung cancer. Modem high-resolution systems are now able to identify many small, potentially cancerous lesions not previously visible in such scans. However, these lesions pose a difficult diagnostic problem; because they are small and peripherally disposed in the lung, they are difficult to reach in order to take a tissue sample. To diagnose cancer, a tissue or cellular sample at a suspect site is often acquired either by transthoracic needle aspiration or during a bronchoscopy procedure. In the bronchoscopic procedure, small forceps, a fine needle, or a cytological brush are advanced through a biopsy channel of a flexible scope and inserted into the major lobes of the affected lung to reach a suspect site that is disposed near a relatively large airway. Current bronchoscopes are only able to fit within the relative large branches of the bronchial system.

Transthoracic needle aspiration is very invasive and is typically reserved for peripheral lung nodules suspected of being cancerous. However, transthoracic needle aspiration can compromise patient health and produce infections. To minimize damage to surrounding tissue and organs, clinicians rely heavily on fluoroscopic C-arms and HRCT to guide the needle to the location of the identified suspect tissue mass. Many procedures are performed while the patient is within the CT suite to enable a biopsy needle to be inserted, steered, and continually re-imaged with a fluoroscope in incremental steps to verify its position relative to a suspected tumor. Unfortunately, transthoracic needle aspiration can compromise patient health and requires prolonged use of imaging systems that impose a substantial financial expense on the patient, and a high time cost on the hospital. Thus, bronchoscopy is a more preferred method of extracting lung tissue for biopsy purposes than is transthoracic needle aspiration.

Bronchoscopy involves the insertion of a fiber-optic bundle into the trachea and central airways in a patient's lung. Navigation of the airway relies on the clinician's ability to direct the scope head into the appropriate region. Histological biopsy samples can be obtained using forceps, a transbronchial needle aspiration, with brush cytology, or by bronchial lavage. Though still invasive, this method is much safer and is not considered to be traumatizing to the patient, in contrast to the transthoracic needle aspiration method. Despite this benefit, the large diameter of commercially available bronchoscopes restricts their entrance into small airways where nodules are commonly found, thus requiring the clinician to either steer the forceps/needle/brush blindly or use fluoroscopy to navigate to these regions throughout the lung in hopes that a representative specimen is obtained from the site actually identified as potentially cancerous.

At present, fluoroscopic C-arms are commonly used in bronchoscopy suites to assist clinicians in navigating the airways by projecting orthogonal views of the thoracic cavity in real-time. Unfortunately, drawbacks of this method are: (1) maneuvering a catheter in two separate planes is perceptually awkward; (2) images provided by a conventional bronchoscope are unclear or "fuzzy" and it is relatively difficult to see anatomical detail; (3) it is cumbersome to continually adjust the C-arm; and (4) the radiation load associated with continued fluoroscopy is detrimental to the health of both the patient and the physician. Also, position coordinates of the bronchoscope cannot be measured or calculated with a fluoroscope, precluding its integration into any graphic interface and making it difficult to keep a historical record of the path followed by the bronchoscope, should such a record be needed during follow up examinations.

An ideal strategy for detection of suspect nodules in the lung would involve a minimally invasive biopsy of the potentially cancerous tissue mass, optical imaging of the epithelial layer, and real-time archiving of examination findings—without the need for expensive, radiation-based imaging systems. Ideally, it should be possible to visually guide a bronchoscope through very small airways, while maintaining a repeatable reference to the location of the bronchoscope in the airways. In addition, it would be desirable to produce data that show the paths followed and the regions of the airways that were visited during the bronchoscopy to enable a physician to easily revisit a specific nodule location at a later time, with minimal time required to retrace the branching path that must be followed to reach that location. The data recorded and stored during such a guided bronchoscopy would enable a physician to contest a charge that the physician failed to take appropriate steps to detect a malignant tissue site in the lungs, should a charge of malpractice arise.

The benefits of visually guiding a device through a lumen in a patient's body are not limited to bronchoscopes or to diagnostic studies of the lung. Clearly, it would also be desirable to guide a flexible endoscope through other body lumens, for example, through a gastric lumen so as to avoid entering the pancreatic duct in a patient when advancing an endoscopic probe beyond the pyloric valve of the stomach. A flexible endoscope might also be more efficiently advanced through the cardiovascular system of a patient if it were possible to visualize the anatomical disposition of the endoscope with reference to its location in a 3-D model of the system as determined with a position sensor. Additionally, an ultra-thin flexible endoscope and position sensor could also be used for navigating through the urethra for an image-guided biopsy of the prostate, which is not possible with conventional endoscopes. Other applications of this technology will undoubtedly be more apparent when its capabilities are fully realized by the medical profession.

SUMMARY OF THE INVENTION

The present invention enables a visually-assisted guidance of an ultra-thin flexible endoscope to a predetermined region of interest through a lumen in a patient's body. This region may be an opacity identified by non-invasive imaging methods, such as HRCT or a malignant lung mass diagnosed in a previous examination. A position sensor on the endoscope produces a signal indicating the position (and orientation) of the distal tip of the endoscope in a Cartesian coordinate system during the procedure. A visual display is continually updated, showing the present position and orientation of the marker in a 3-D graphical surface model of the airways that is generated through segmentation of medical images. The visual display also includes windows depicting a virtual fly-through perspective and real-time video images acquired at the distal tip of the endoscope, which can be stored as data. Optionally, an audio or textual account can be included with data and stored for subsequent review.

In addition to the surface model, an airway tree model is constructed to outline the hierarchy and connectivity of bifurcations originating at the main carina and extending down the bronchial tree. Within this airway tree model, branch points are represented by their 3-D position, a generation index that specifies how many levels separate the node from the main carina, the branching angles of the two subtending vessels, and a definition of the centerlines that connect two linked branch points. Based on the known position of potentially cancerous lesions on a HRCT scan, a number of nearby biopsy points are selected for inspection. From these points, a series of courses are automatically plotted in the model tree to effectively steer the physician at each branching while recording and graphically indicating regions previously inspected during the procedure to prevent over-sampling of the same region as well as ensuring a comprehensive probing of potentially affected areas.

The identification of bifurcations by the clinician on video images serves to confirm that the measured real-time position of the scope head aligns with its inferred position on the visual 3-D model and continually recalibrates the two to reduce accumulating errors. Recalibration involves a point to point re-registration of the lung model bifurcation location to the known position of the tracker in 3-D space. As a result, the position of the scope within a set of tightly branched vessels can be deduced using knowledge of the decision history where a decision constitutes the protrusion of the scope into one of two or more daughter vessels at any given carina.

Accordingly, one aspect of the present invention is directed to a system for visually guiding a flexible endoscope through linked passages within a body. The system includes a signal source that emits a reference signal useful for spatially tracking the progress of the flexible endoscope through the linked passages, and a sensor that produces an output signal indicating a 3-D disposition of a distal end of the flexible endoscope using the reference signal of the signal source. The signal source can either be included adjacent to the distal end of the flexible endoscope or can be disposed external to a patient's body. If the signal source is external, the sensor is disposed adjacent to the distal end of the flexible endoscope, while if the signal source is mounted on the flexible endoscope, the sensor is disposed externally. A user interface is included for displaying a view from within the linked passages as the flexible endoscope is advanced therethrough. The displayed image enables the flexible endoscope to be visually guided and tracked along a path being followed through the linked passages.

The system preferably employs a 3-D model of the linked passages that is used to assist in determining at least an initial path along which to advance the flexible endoscope. The 3-D model is preferably derived from an image of a portion of a body in which the linked passages are disposed, for example using the images produced by a CT or MRI scan. This model provides an indication of an orientation and a disposition of the linked passages relative to a specific anatomical feature, such as the carina in the lungs, a bone structure, or another known easily-identified feature.

While it is possible to use long wavelength infrared signals that penetrate tissue to track the flexible endoscope, the signal source preferably comprises an electromagnetic field source. In this case, the sensor preferably comprises at least three coils configured to sense at least a 3-D position of a distal portion of the flexible endoscope relative to the electromagnetic field source. The sensor comprises at least two coils configured to sense both a 3-D position and an orientation of the distal portion of the flexible endoscope in six degrees of freedom. Only one coil is needed if it is desired to track position and orientation of the flexible endoscope in five degrees of freedom, as it is advanced through the linked passages.

Optionally, the system also includes a body function sensor configured to be disposed adjacent to either the sternum, the thorax, and the mouth of a patient, to monitor one or more of breathing, chest orientation, and the deformation of the lungs of a patient. This sensor produces data that can be employed for updating the 3-D model in regard to changes caused by a body function. Also, the signal from this sensor is useful for determining the disposition of the distal end of the flexible endoscope in regard to the at least one body function, or for gating the flexible endoscope to synchronize with the body function when sensing the position/orientation of the flexible endoscope, thereby minimizing the effect of the body function.

In a preferred embodiment, the flexible endoscope includes a vibrating optical fiber that scans a region adjacent to the distal end of the flexible endoscope, producing a signal that is used to drive the display. This configuration is very compact, yet produces much higher resolution images than is possible with prior art optical fiber endoscopes.

Other aspects of this invention are directed to a flexible endoscope, generally as described above, and to a method for guiding a flexible endoscope through linked passages to either perform a diagnostic procedure or reach a desired location in a patient's body, while tracking the disposition of a distal end of the flexible endoscope. The method includes the step of using the flexible endoscope for scanning a region of the linked passages that is adjacent to the distal end of the flexible endoscope, to display an image of the region. An external tracking signal is employed and serves as a reference relative to the linked passages within the patient's body. The method thus includes the step of tracking the disposition of the distal end of the flexible endoscope as it is advanced through the linked passages, using an output signal produced in response to sensing the external tracking signal adjacent to the distal end of the flexible endoscope. The distal end of the flexible endoscope is then advanced through the linked passages along a path determined at least in part by the image of the region and by the output signal, to reach the desired location in the patient's body. Other steps of the method are generally consistent with the function of the system discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIGS. 1A and 1B are, respectively, a functional block diagram of the flexible endoscope system, and a cross-section of a rigid, distal end of a flexible endoscope that includes optical fibers for conveying light back to detectors (not shown) at a proximal end of the flexible endoscope, where the light was emitted by the scanning optical fiber and reflected by an adjacent surface back into the optical fibers;

Figure 3B:
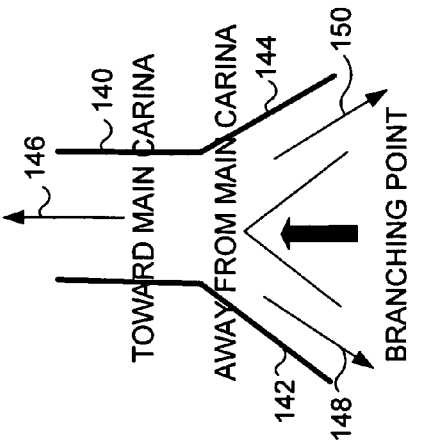
Figure 3A:
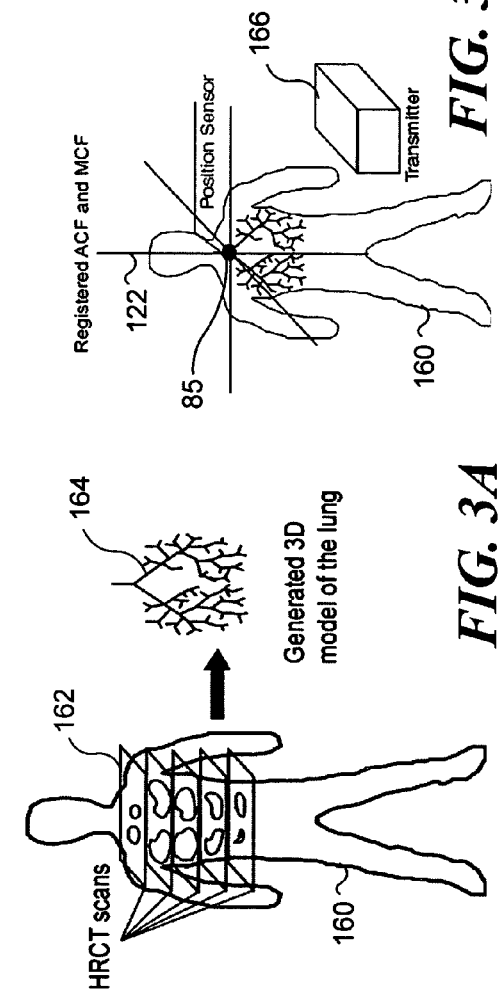
Figure 4A:
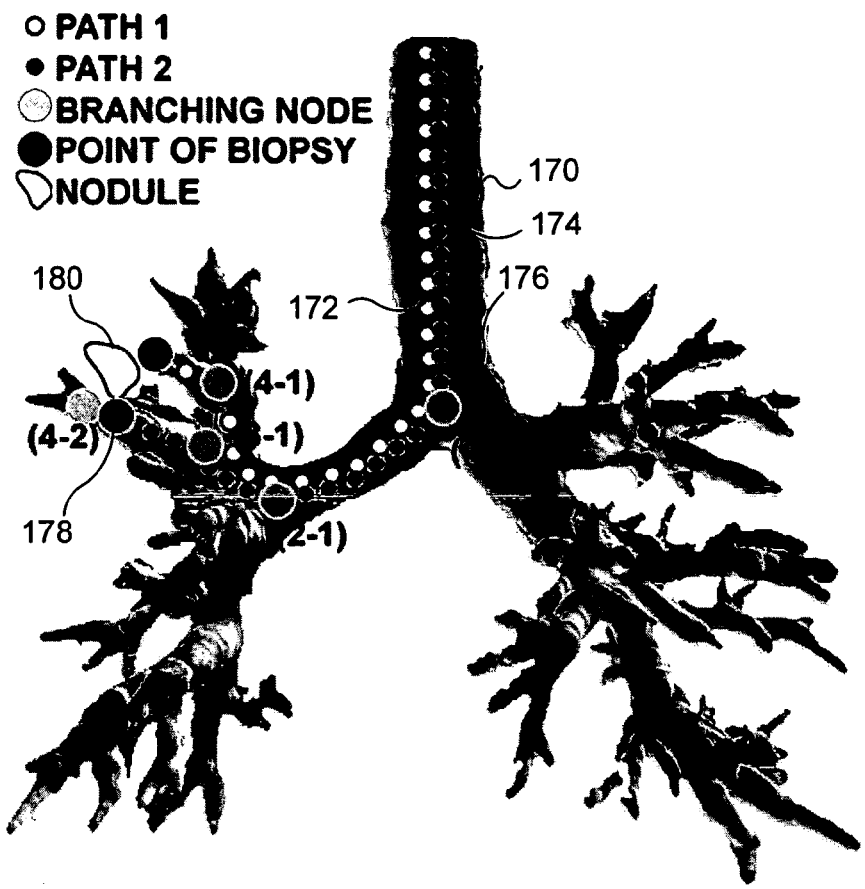
Figure 4B:
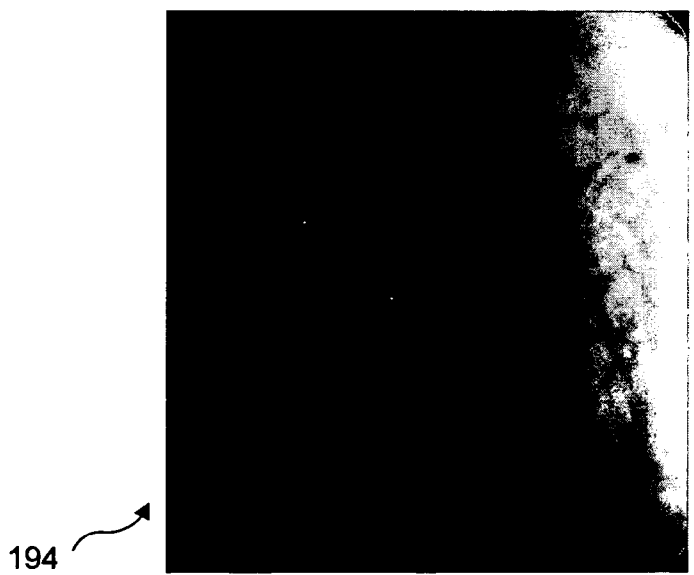
Figure 4C:
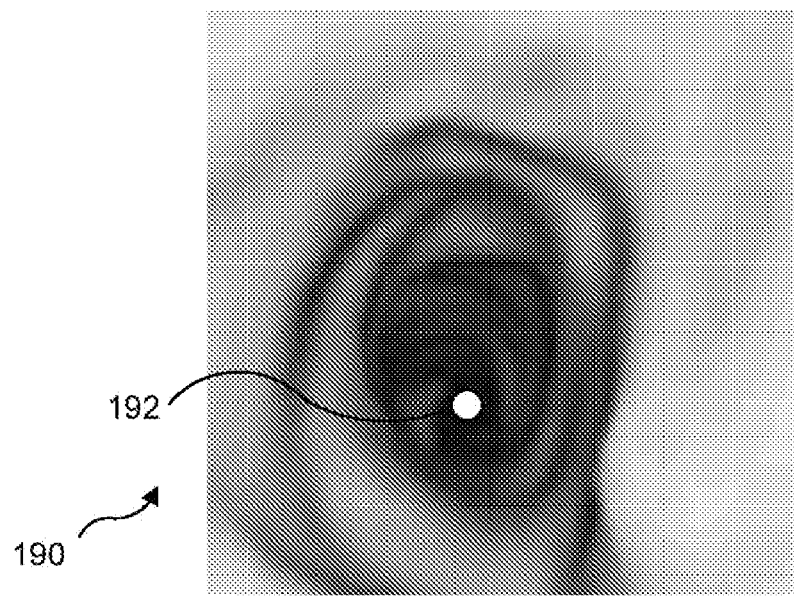
Figure 4D:
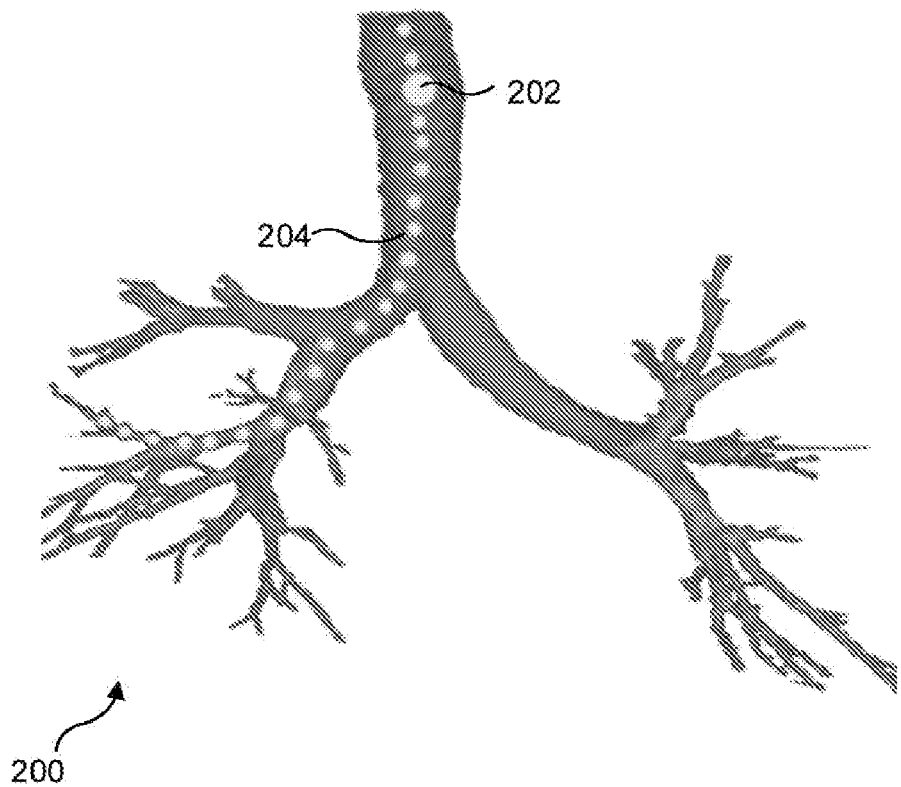
Figure 5A:
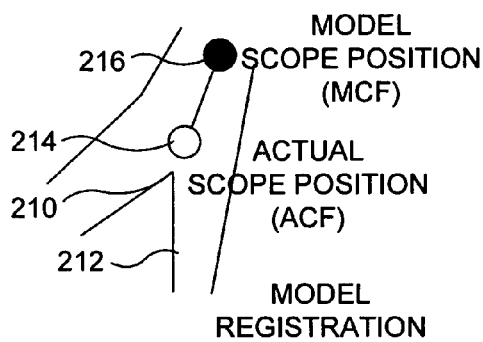
Figure 5B:
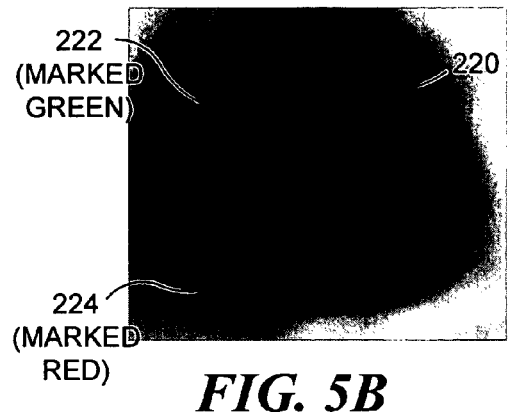
Figure 5C:
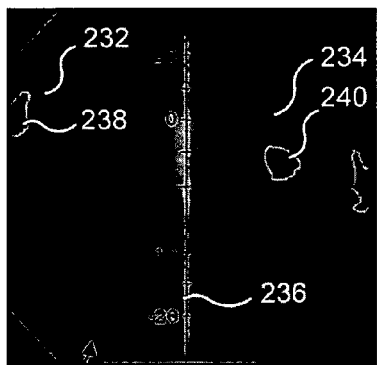
Figure 5D:
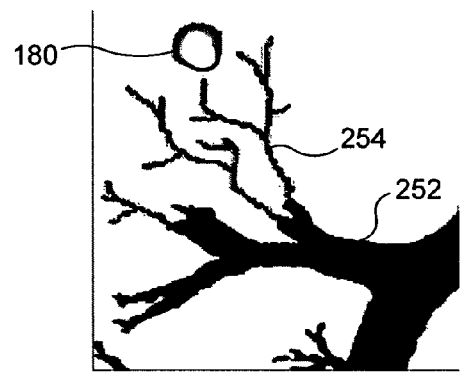
Figure 6:
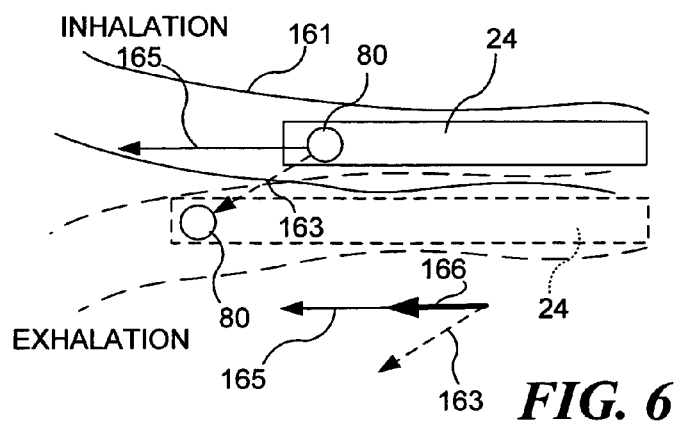
Figure 7A:
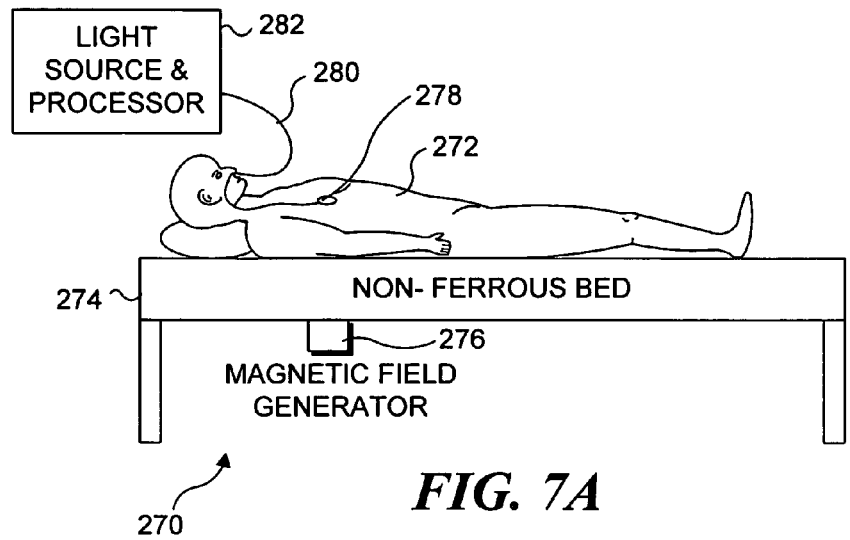
Figure 7B:
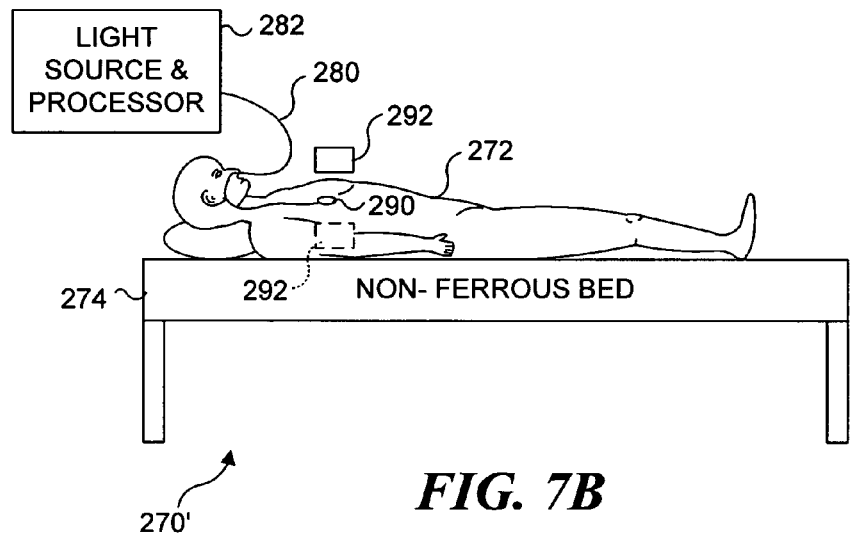
Figure 7C:
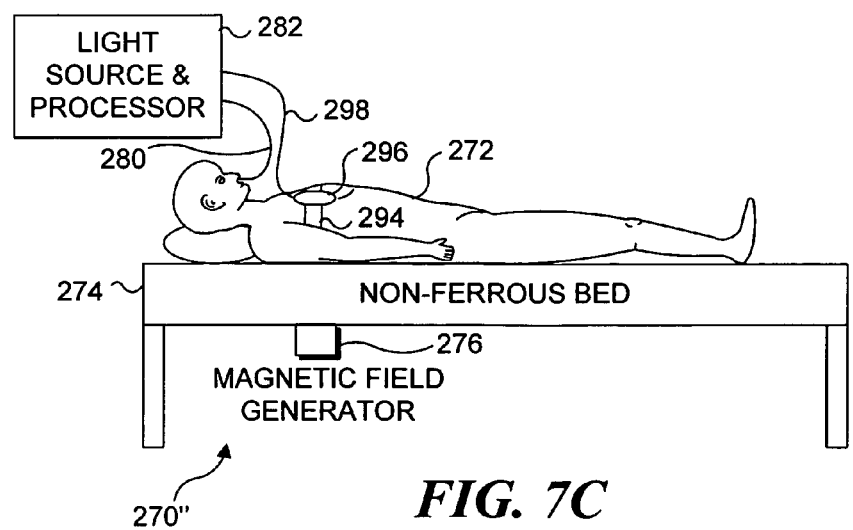
Figure 7D:
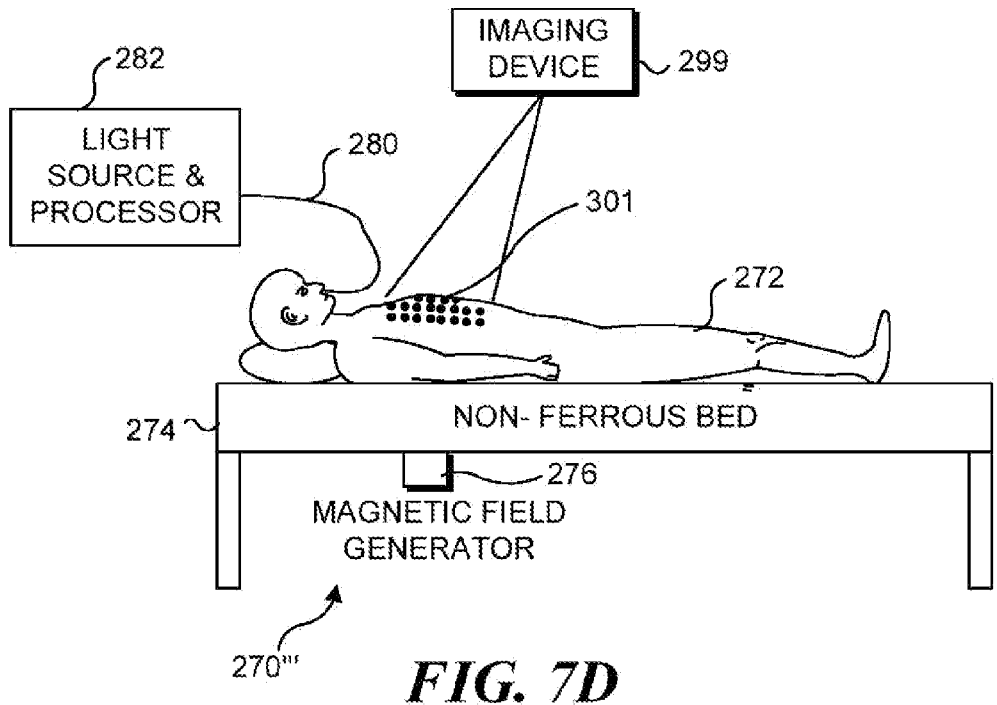
Figure 7E:
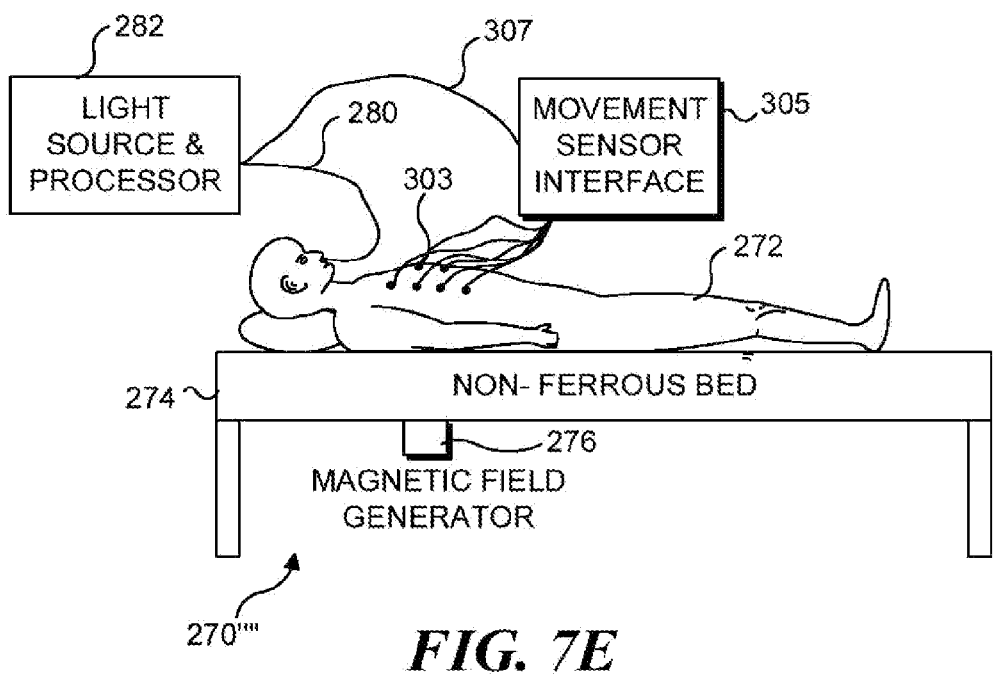
Figure 8A:
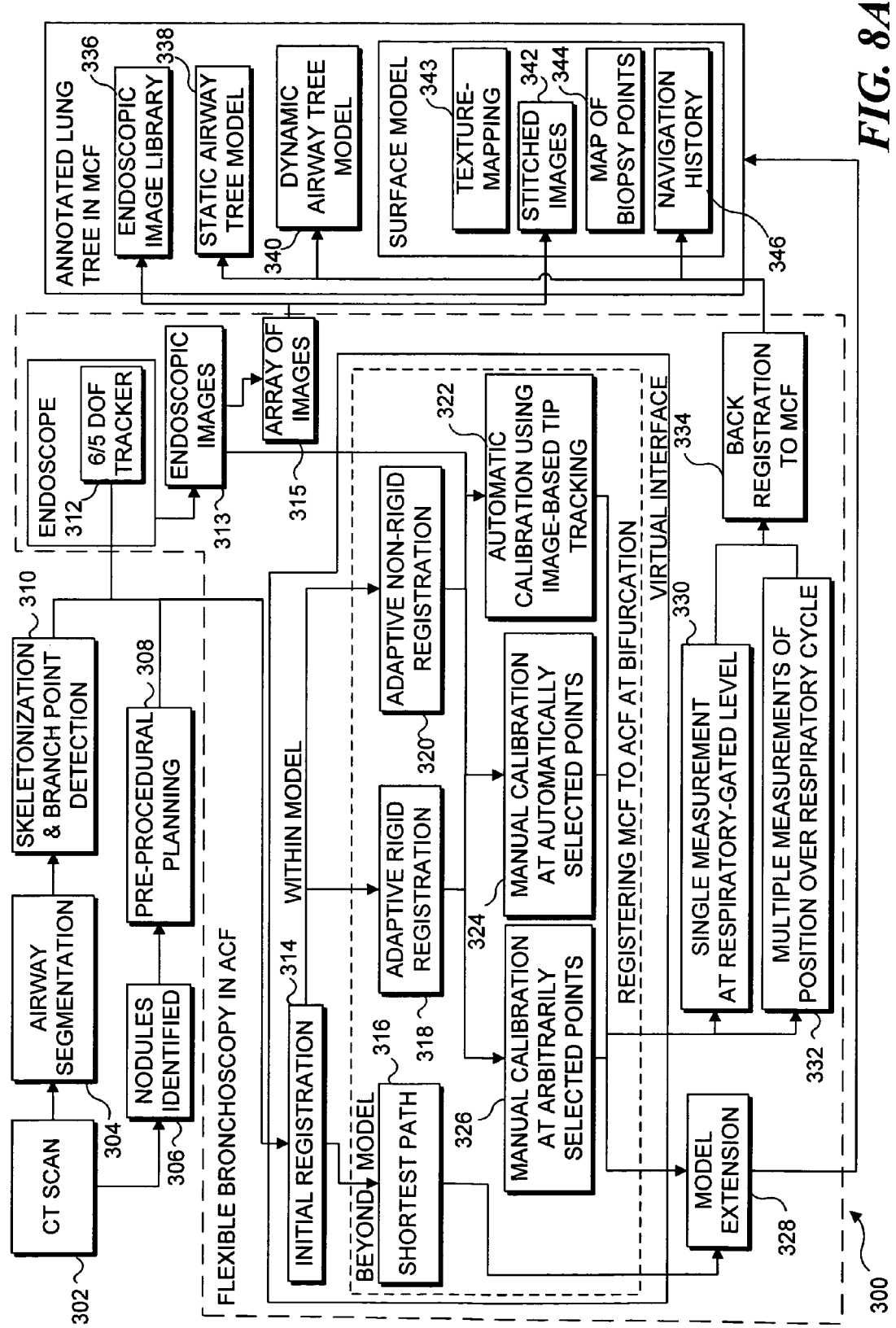
Figure 8B:
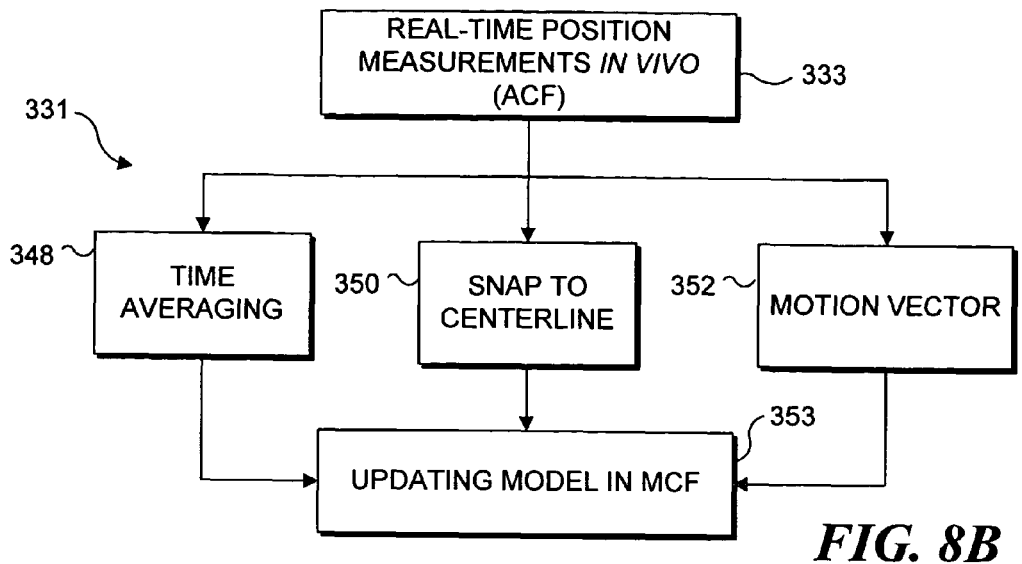
Figure 8C:
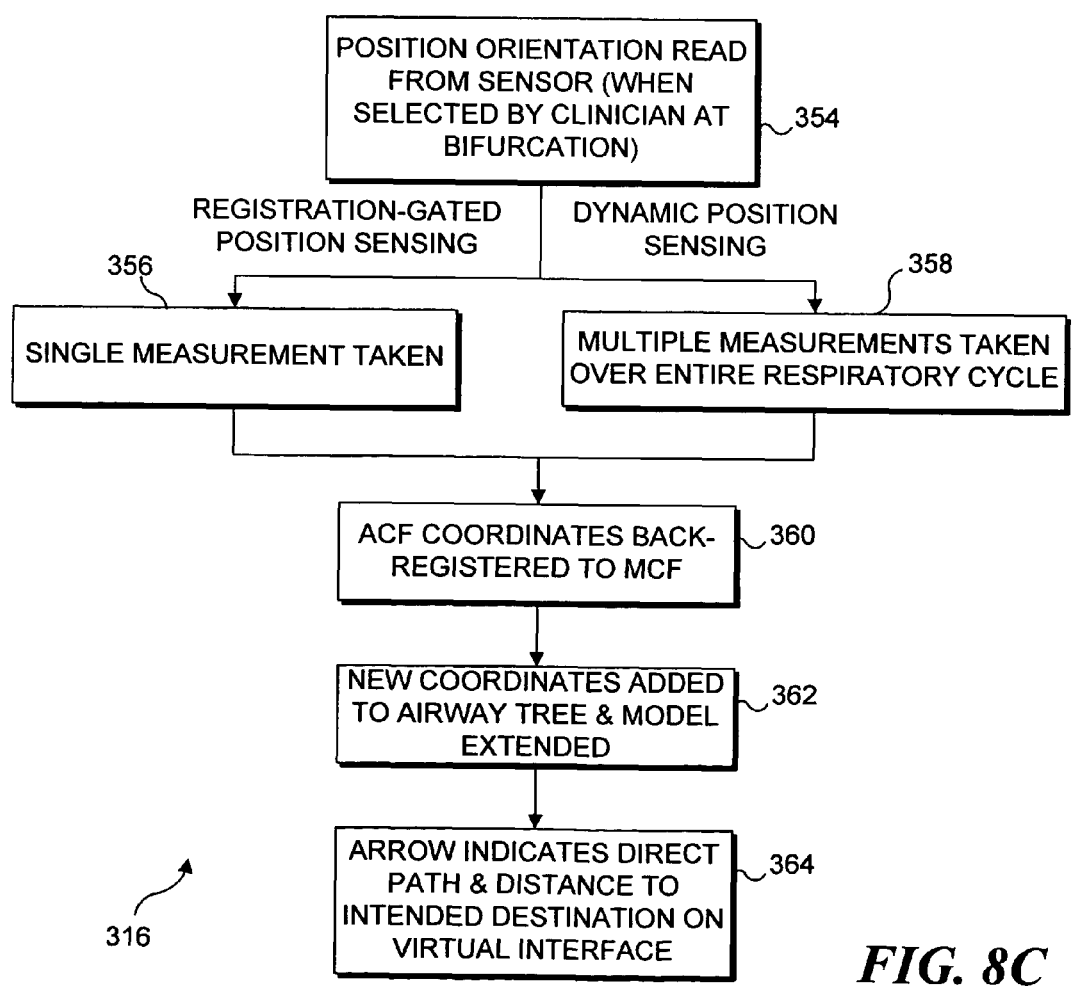
Figure 8D:
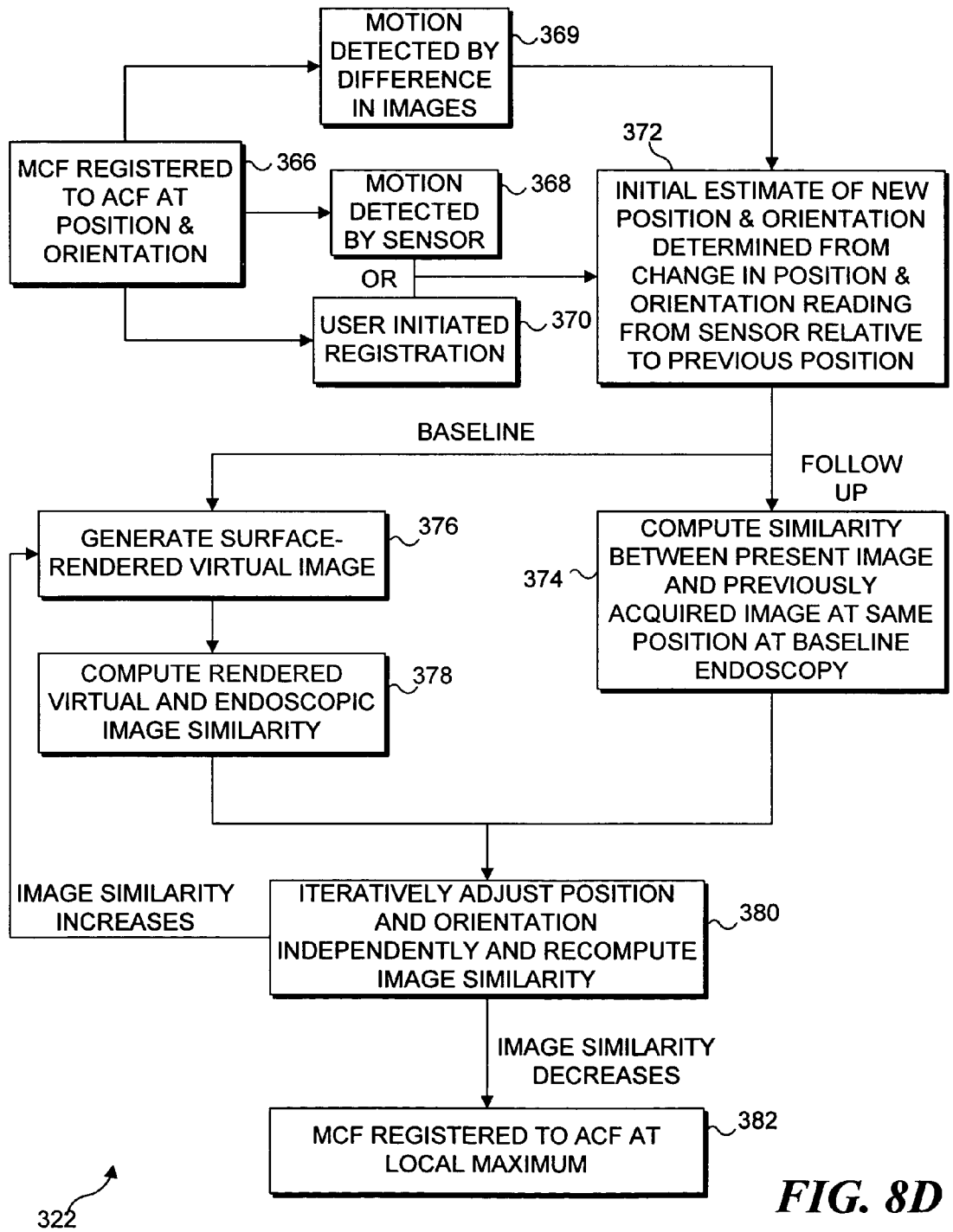
Figure 8E:
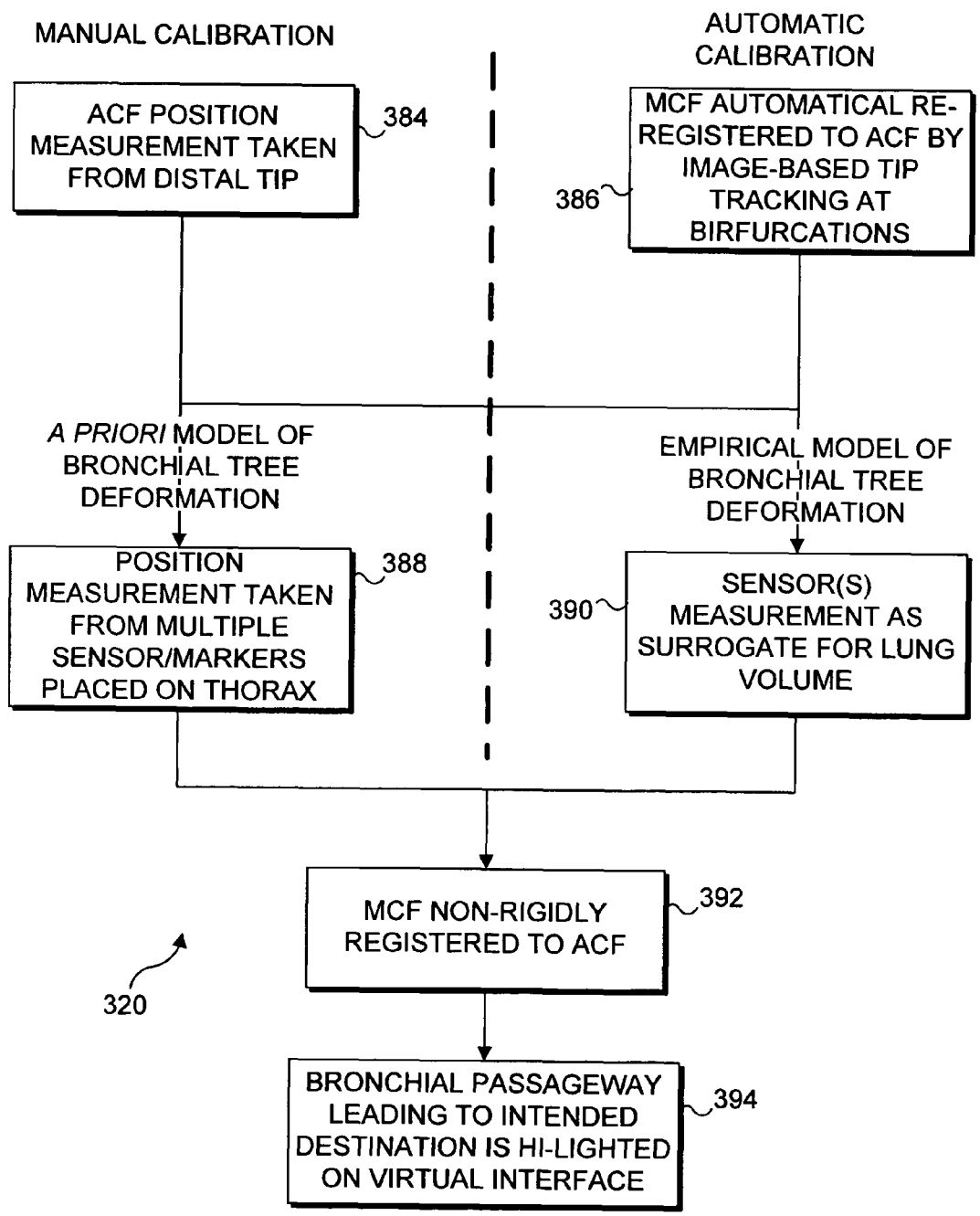

FIG. 2-D is a schematic of an airway surface model with an overlay of an airway tree model, showing how a detected branch point is projected to an inner point of confluence of the surface model for manual reregistration at automatically selected points;

FIG. 3A is a schematic view of an airway tree model generated from a series of transverse HRCT scan slices;

FIG. 3B is a schematic view of a calibration of a position sensor used on a flexible endoscope in accord with the present invention, by selecting the main carina as the origin (i.e., a reference point), and using a magnetic field transmitter to measure position and orientation relative to the reference point;

FIG. 4A is a constructed airway surface model, showing selected points targeted for a biopsy, and an automated course planning through the lung passages (where the generation index of each branch point is indicated);

FIGS. 4B, 4C, and 4D are, respectively, an exemplary user interface depicting a real-time image of a bronchial passage produced by the flexible endoscope, a virtual analog of the same perspective constructed from HRCT scans, and a static 3-D airway surface model in which a present course or path is plotted along the centerlines of the airway tree model passages, along with a current position of the flexible endoscope;

FIG. 5A is a schematic diagram showing how the 3-D model is calibrated to adjust for an accumulated error by comparison of the model with the actual position of the distal end of the flexible endoscope;

FIG. 5B illustrates how color coding is employed to mark airways that have already been inspected, e.g., with a red marker, and an intended course of navigation, with a green marker;

FIG. 5C is an image illustrating segmentation of low light intensity regions of subtending vessels and an axis showing 2-D deflection angles;

FIG. 5D illustrates how a 3-D model is extended by mapping a position of the flexible endoscope on the model coordinates at open vessel terminations;

FIG. 6 illustrates an example showing how motion vector correction is applied by assuming forward movement of the flexible endoscope, to account for tidal breathing in the small lung passages;

FIG. 7A illustrates a system in accord with the present invention in which an external electromagnetic field generator is employed as a signal source, for determining a position of an internal sensor disposed adjacent to the distal end of the flexible endoscope;

FIG. 7B illustrates a system in accord with the present invention in which an internal electromagnetic field source adjacent to a distal end of the flexible endoscope is employed with an external sensor, for determining a position of the distal end of the flexible endoscope;

FIG. 7C illustrates a system in accord with the present invention in which a sensor is disposed around the thorax of a patient to monitor breathing, so that errors in the position of the distal end of the flexible endoscope can be compensated for the effects of breathing and other physiological body functions;

FIG. 7D illustrates a system in accord with the present invention in which an imaging device is shown imaging a plurality of markers applied to the chest of a patient to monitor breathing and movement, so that errors in the position of the distal end of the flexible endoscope can be compensated;

FIG. 7E illustrates how a plurality of motion sensors affixed to the thorax of a patient can be used to provide bodily function signals that can be employed to compensate for movement of the patient's lungs and bronchial passage;

FIG. 8A is a flowchart showing the logical steps employed in the present invention;

FIG. 8B is a functional block diagram illustrating the different methods that can be employed to update the 3-D model;

FIG. 8C is a flow chart illustrating details of the step for using the shortest or most direct path to navigate when moving beyond the extent of the 3-D model;

FIG. 8D is a flow chart illustrating details of the step for automatically tracking position in the MCF and re-registering to the ACF using the endoscopic images at a bifurcation of the passages;

FIG. 8E is a flow chart illustrating details of the step for adaptive non-rigid registration of the MCF and ACF;

FIG. 8F is a flow chart illustrating details of the step for adaptive rigid registration of the MCF and ACF;

FIG. 9A is a schematic diagram of a dipole electromagnetic field transmitter and sensor capable of sensing six degrees of freedom of the distal end of the flexible endoscope;

FIG. 9B is a schematic diagram of a sensor with two coils that is capable of sensing six degrees of freedom of the distal end of the flexible endoscope; and FIG. 9C is a schematic diagram of a sensor with a single coil that is capable of sensing five degrees of freedom of the distal end of the flexible endoscope.

DESCRIPTION OF PREFERRED EMBODIMENTS

Ultra-Thin Flexible Endoscopes

Ultra-thin flexible endoscopes have been devised for diagnostic imaging of small lumens with diameters similar to regions in the peripheral lung (i.e., with diameters less than 3 mm). A flexible endoscope of this capability has been achieved mainly by reducing the number of fibers contained within the imaging bundle. The disadvantage of this solution is that in removing fibers, the resolution and field of view are greatly diminished. Space restrictions preclude incorporation of a biopsy channel into the design. Although quite thinner than their predecessors, these flexible endoscopes also remain fairly expensive and often break at small bending radii. The poor imaging ability, fragility, expense, and inability to obtain tissue specimens deters the use of this type of bronchoscope for examination of masses in the peripheral lung.

The development of a 2 mm diameter flexible endoscope in accord with the present invention enables clinicians to access peripheral airways of the lung to biopsy nodules identified on HRCT images. Embedded within a preferred embodiment of the flexible endoscope is a single-mode optical scanning fiber offering a wide angle field of view, as well as a wired position-sensor that is used to locate the distal tip of the catheter in 5 or 6 degrees of freedom, with an accuracy of around 1 mm. While this technology permits extension of this device to more distant regions of the lung, it becomes imperative that some guidance system be incorporated to assist in navigating this flexible endoscope through pathways potentially leading to the region of interest.

Motivation for Position Tracking

The lung is a series of bifurcating airways ranging in diameter from 18 mm to 0.25 mm. Conventional fiber bundle bronchoscopes designed primarily for larger lumens are capable of reaching $5^{th}$ generation bronchioles amounting to a total of $2^5$ or 32 separate airways. The ultra-thin flexible endoscope is able to extend to the $8^{th}$ generation comprising a total of $2^8$ or 256 distinct airways. Though navigation of these devices typically relies on an optical view from the head of the scope, this does not necessarily aid in directing the catheter through a system where there is extensive branching. The exponential increase in complexity underscores the need for some means of visually tracking the position of this endoscope on a HRCT generated 3-D model so that it may effectively guide the physician at each branch point as well as recording the regions that have been inspected. By implementing a guidance system within the ultra-thin flexible endoscope mentioned above, procedures can be performed easily within general examination rooms without need for C-arm fluoroscopy units, CT or MRI scanners, and the highly specialized environments that occupy these systems.

Position Tracking

A position tracker serves as a 3-D guidance system by providing absolute measurements of the tracker's position with reference to some external source. The three orthogonal coils that constitute the sensor generate voltages when placed within a magnetic field. These signals can be measured and digitized to determine position within six degrees of freedom. Magnetic field position sensors have diminished in size over the years, promoting their use in many medical applications where virtual navigation has eliminated the need for radiation-based imaging methods. Miniature sensors have been embedded in electrophysiology catheters used for cardiac navigation and arrhythmia treatment (CARTO XP™, available from Biosense Webster of Diamond Bar, CA). Similar systems use electric potential to measure position (Localisa™ from Medtronic of Minneapolis, MN; and EnSite NavX™ from Endocardial Solutions of St. Paul, MN). Overall, these systems are used for modeling voltage potentials in the heart and are not concerned with traversing tortuous branches or with path finding. Because these catheters contain electrodes rather than imaging optical fibers, their design restraints are far less stringent. However, the present invention has established the use of electromagnetic and electric potential tracking systems as a reliable means for measuring position *in vivo*, within a clinical setting. As well, the system components used in the present invention are far more accessible and inexpensive than fluoroscopy units, CT scanners, MRI apparatus, or other large imaging systems that are often immobile or at least difficult to move, occupy a large space, require specialized suites and technicians, and require considerable maintenance to keep operational.

Unfortunately, position itself is not sufficient for navigating a catheter through a series of diverging passages such as the bronchial airways of the lung. Sources of error, such as inaccurate readings, poor morphological correlation with the static 3-D model, patient movement, breathing, deformation induced by the catheter, or other perturbations may be too great to ascertain the location of the catheter tip within one of many small bronchial passageways.

One aspect of the present invention is directed to a system for supervised steering of a flexible endoscope through the bronchial tree. The system relies on the visual identification of branch points by a physician, to continually recalibrate the current position of the flexible endoscope to the corresponding branch point on the static 3-D model. This methodology uses measurements of absolute position relative to a sensor, in order to generate positional data comprising a device "history" that simplifies the position of the flexible endoscope to a series of choices made along a binary decision tree in which the decisions determine which branch to take with the flexible endoscope at each junction of the bronchial tree. Incorporated within this framework are several approaches for reducing the measurement error, given the number of perturbations to the system. A simplified decision algorithm is also described for piloting the flexible endoscope to regions within small airways that are missing in the reconstructed model, due to the limited image resolution and partial volume effects associated with CT scanning.

However, it must be repeatedly emphasized that the present invention is not limited only to traversing bronchial passages, since the present invention can be employed for traversing other types of linked passages within a patient's body, besides those in the bronchial system. The same approach is used in almost any such application of the present invention, for guiding the flexible endoscope through the linked passages. Accordingly, although the focus of this disclosure is directed to the use of the system for navigating a flexible endoscope through bronchial passages, the discussion presented herein should be understood to apply to many other applications of this invention.

Details of the Flexible Endoscope System

Figure 1A:
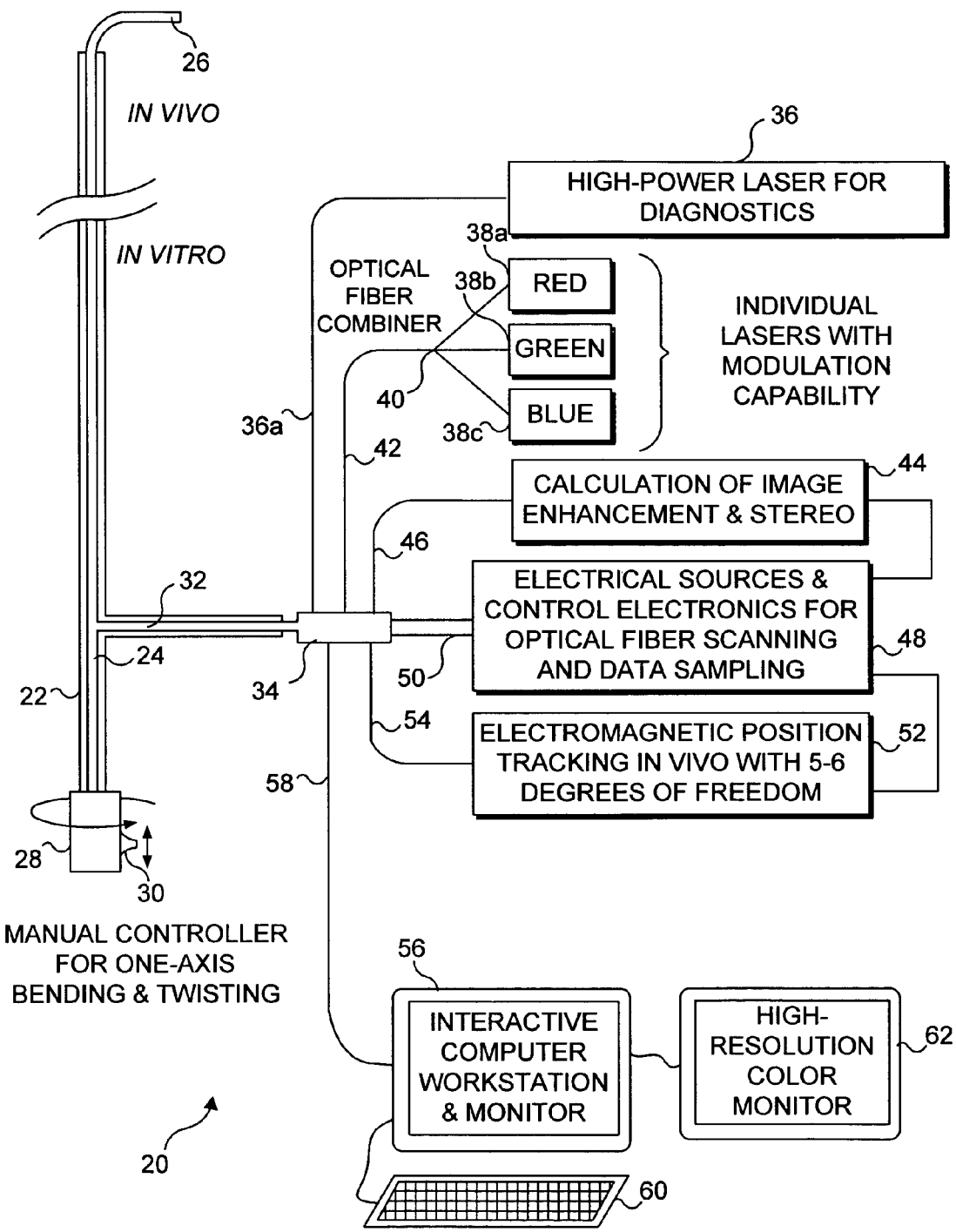
FIGS. 1C and 1D are, respectively, a perspective schematic view and an end view of a distal portion of a flexible endoscope that includes Red, Green, Blue (RGB) light sensors for sensing light that has been emitted by a scanning optical fiber and which has been reflected from an adjacent surface.
FIG. 1E is a schematic cross-sectional view of the distal end of a flexible endoscope that includes a triangular mirror that responds to parallel polarized or scattered light, and to perpendicular polarized or fluorescent light received from surfaces adjacent to opposite sides of the distal end of the flexible endoscope.
FIG. 1F is a schematic cross-sectional view of the distal end of another embodiment of the flexible endoscope that includes a biopsy channel and a biopsy needle within the channel that can be selectively advanced into tissue to take a sample.
FIGS. 1G and 1H are, respectively, a schematic transverse cross-sectional view near the proximal end and a schematic transverse cross-sectional view of the rigid portion (near the distal end) of the flexible endoscope of FIG. 1F.
FIG. 1I is a schematic view of another embodiment that includes a cytological brush for taking a biopsy sample (for purposes of simplifying the image, much of the detail is omitted in this Figure)

An exemplary flexible endoscope system 20 is illustrated in FIG. 1A. In a system, a flexible endoscope 24 is inserted through a multi-function endoscopic catheter 22, which facilitates accessing passages of interest within a patient's body, such as the bronchial passages within the lungs. Flexible endoscope 24 includes a relatively rigid portion 26, which is disposed at its distal end; details of several different embodiments of the flexible endoscope are discussed below, particularly in regard to the components used for scanning and imaging tissue that is adjacent to the distal end of the flexible endoscope. The proximal end of the flexible endoscope includes a rotational control 28 and a longitudinal control 30, which respectively rotate and move the flexible endoscope longitudinally relative to catheter 22, providing manual control for one-axis bending and twisting. Various electrical leads and/or optical fibers (not separately shown) extend through a branch arm 32 to a junction box 34.

Light for scanning tissue at the distal end of the flexible endoscope can be provided either by a high power laser 36 through an optical fiber 36*a*, or through optical fibers 42 by individual red, green, and blue lasers 38*a*, 38*b*, and 38*c*, respectively, each of which can be individually modulated and the colored light combined into a single optical fiber 42, using an optical fiber combiner 40. A signal corresponding to light that is reflected from tissue adjacent to the distal end of flexible endoscope 24 can either be detected with sensors disposed adjacent to the distal end, or can be conveyed through more optical fibers that extend back to junction box 34.

This signal is processed by several components, including a component 44 that is connected to a junction box 34 through leads 46 and which calculates image enhancement and provides stereo imaging of the scanned region. Also provided are electrical sources and control electronics 48 for optical fiber scanning and data sampling, which are coupled to junction box 34 through leads 50. A sensor (not shown in this figure) provides signals through leads 54 that enable electromagnetic position tracking of the distal end of the flexible endoscope in vivo, indicating its position (and optionally, its orientation) with up to five to six degrees of freedom, as indicated in a block 52.

Leads 58 connect junction box 34 with an interactive computer workstation and monitor 56, which has a keyboard and/or other user input device 60. Optionally, the interactive computer workstation is connected to a high resolution color monitor 62, which can display very detailed video images of the passage through which the flexible endoscope is being advanced.

Embodiments of Flexible Endoscope

Figure 1B:
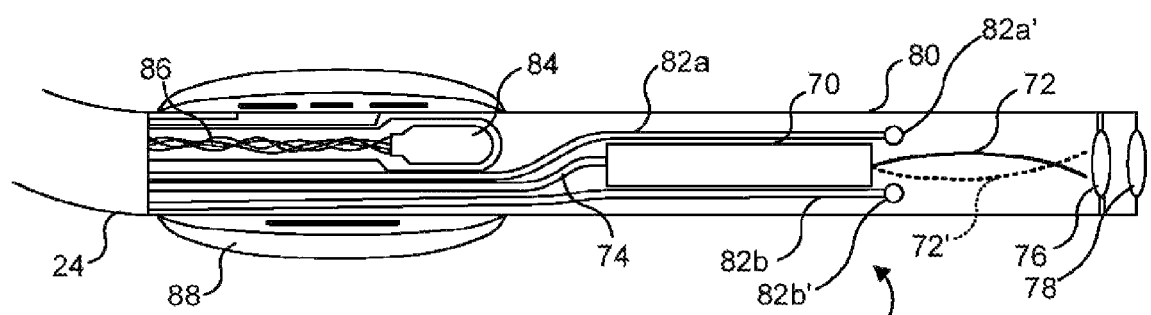

In the best scenario, the implementation and operation of this navigation scheme relies on several components, including a static 3-D graphical model of the airspaces, a forward viewing bronchoscope or flexible endoscope with a digital video output, a monitor, a processor, and appropriate software to carry out the processing for implementing the steps of the navigation scheme in its various embodiments. This invention was designed particularly to employ a novel ultra-thin flexible endoscope such as shown in FIGS. 1B, 1C and 1D, and 1E. Each of these embodiments includes a housing 80 (FIG. 1B), 80' (FIGS. 1C and 1D), and 102 (FIG. 1E) having an outer diameter of about 2 mm or less. This small diameter permits extension of the device into previously inaccessible regions of the lung or other body passages where there is extensive branching, requiring a tracking method to determine the location of the flexible endoscope in the passage. However, this invention can also be very useful when the flexible endoscope is advanced through any passage in which branching occurs. A wired position sensor 84, which disposed adjacent to the distal end of a flexible endoscope 24, as shown in FIG. 1B, measures the orientation and position within five or six degrees of freedom in connection with a system 20, as illustrated in FIG. 1A.

Flexible endoscope 24, which is shown in FIG. 1B, includes a position sensor 84 with three orthogonal coils (not separately shown) that produce signals indicative of the position and orientation of rigid portion 26 of the flexible endoscope relative to an electromagnetic field source (not shown in this Figure), which is external to the patient's body in this embodiment. The signals produced by the sensor are conveyed through electrical leads 86 to the interactive computer workstation and monitor, which processes the signal to determine the absolute position and orientation of the distal end of flexible endoscope 24 relative to the electromagnetic field source. The signal indicative of position and orientation thus enables the user to determine where the distal end of the flexible endoscope is located in regard to a 3-D coordinate system based upon the location of the electromagnetic field source.

Optionally, a balloon 88 can be inflated to stabilize the flexible endoscope within a passage of the patient's body. When balloon 88 is inflated, the flexible endoscope is held in place, which can resist movement of the distal end when a biopsy needle is inserted and retracted or can stabilize the flexible endoscope so that the movement of air through the bronchial passages does not displace it.

A key advantage of the present invention is that the user can view the path being followed by the flexible endoscope through linked passages in the patient's body, by displaying the video images produced by a scanning optical fiber 72, which is disposed in the rigid portion at the distal end of the endoscope. The scanning optical fiber in this embodiment is driven to move in a spiral scan by a two-axis piezoelectric driver 70. Light is conveyed through a single mode optical fiber 74 to the scanning optical fiber from an external laser or other light source and is directed first through a lens 76 and then through a lens 78. These two lenses focus the light emitted by the scanning optical fiber onto an adjacent surface. Light reflected from the adjacent surface passes back through lenses and is conveyed to multimode optical fibers 82*a* and 82*b*, which respectively include lenses 82*a*' and 82*b*', back to the proximal end of the flexible endoscope, where light detectors (not shown) are provided, or alternatively, the detectors can be included in the rigid portion of the endoscope, so that electrical signals from the light detectors are conveyed through electrical leads (running generally like multimode optical fibers 82*a* and 82*b*, but much smaller in diameter) to the processing hardware that is external to the patient, enabling a video image of the region through which the flexible endoscope is moving to be viewed by the user.

Figure 1C:
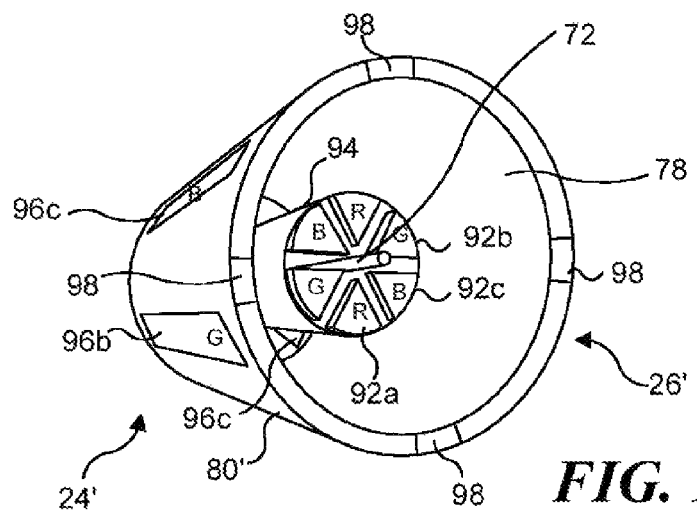
Figure 1D:
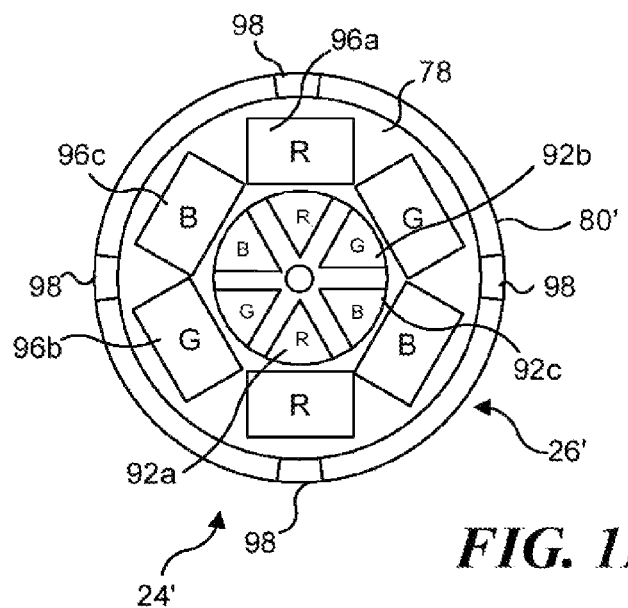

FIGS. 1C and 1D illustrate flexible endoscope 24', which is much like flexible endoscope 24, except that a rigid portion 26' includes red light detectors 92*a*, green light detectors 92*b*, and blue light detectors 92*c* spaced closely around scanning optical fiber 72 at the end of a support cylinder 94, and more radially outwardly disposed red light detectors 96*a*, green light detectors 96*b*, and blue light detectors 96*c* that are set back from lenses 76 and 78. These sensors, which are each sensitive to a specific spectral range (e.g., a specific color of light), can comprise a photodiode material with an appropriate filter cap. The redundant light detectors of each color are provided so that ambient light levels can be recorded and specular reflections can be excluded in the image that is detected in response to light reflected from adjacent tissue by excluding the detector of each color that has the substantially higher level output, which is the light detector that is receiving specular reflection from the tissue rather than diffusely reflected or scattered light.

Also shown in FIGS. 1B and 1C are touch sensors 98 that are spaced apart around the periphery of lens 76. Touch sensors 98 comprise capacitive or piezoelectric sensors that respond to contact with tissue, e.g., at the junction of two passages that branch off of the passage in which the flexible endoscope is being advanced. The signal produced by touch sensors 98 is thus useful in determining when the distal end of the flexible endoscope has contacted the junction, which serves as reference for tracking the flexible endoscope and providing registration between the MCF and ADF.

Figure 1E:
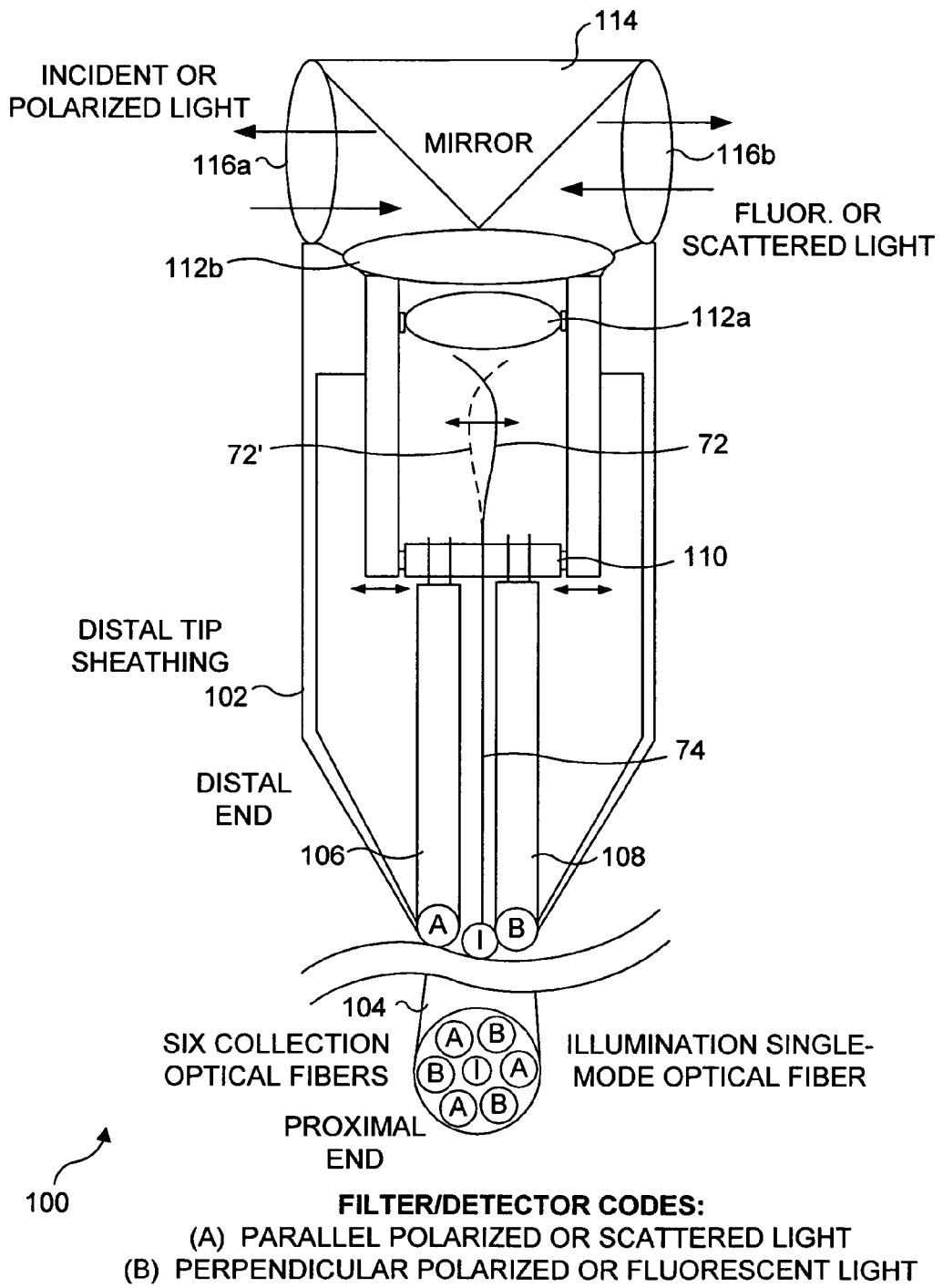

In FIG. 1E, a flexible endoscope 100 is illustrated that is capable of imaging adjacent regions to the sides of the flexible endoscope, and as shown in the example, using different light modalities. This embodiment thus transmits scanning light transversely of the longitudinal axis of distal tip sheath or housing 102 and receive light reflected back from the adjacent tissue to the sides of the distal end of the flexible endoscope. Specifically, in addition to single mode optical fiber 74, which is used to convey light to illuminate the regions on opposite sides of the housing as scanning optical fiber 72 moves in a spiral mode, flexible endoscope 100 also includes three collection optical fibers 106 that convey either parallel polarized light or scattered light collected from adjacent tissue disposed to the side of the housing, and three collection optical fibers 108 that convey either perpendicular polarized light or fluorescent light from adjacent tissue on the opposite side of the housing. The proximal ends of these optical fibers are illustrated at a proximal end 104 of the flexible endoscope, where appropriate filters (not shown) might be applied, as appropriate. The distal ends of the collection optical fibers are secured in a mount 110 to receive light that is reflected through lenses 112a and 112b, having passed through lens 116a or lens 116b and been reflected from a triangular or pyramidal-shaped mirror 114. The light emitted from scanning optical fiber 72/72' is also focused by lenses 112a and 112b, as well as one of lenses 116a and 116b (depending upon which side of triangular-shaped mirror 114 the light is incident and reflected). If a pyramidal-shaped mirror 114 is employed, lenses (not shown) could be included on the side facing into the drawing and on the side facing up in the drawing, to collect light from those two sides, as well as from the two sides that are shown.

Figure 1F:
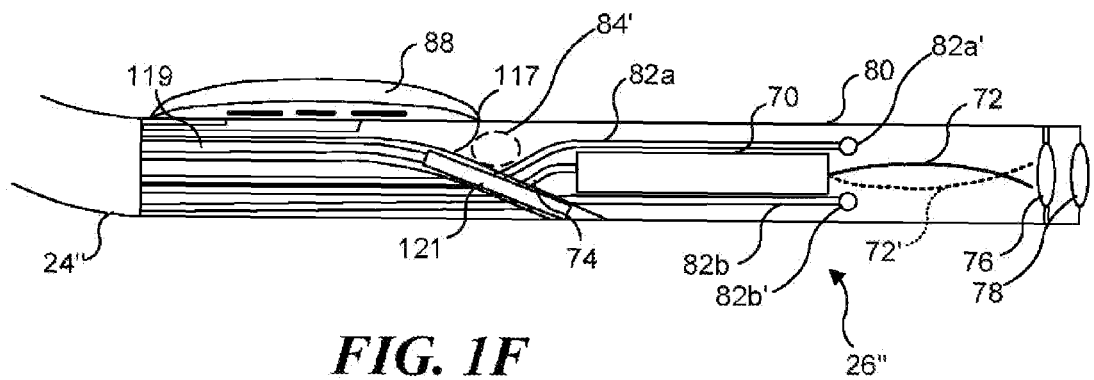
Figure 1G:
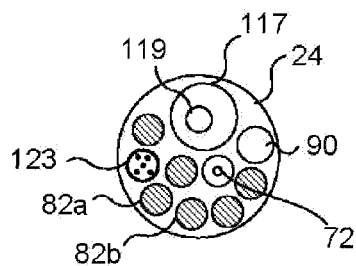
Figure 1H:
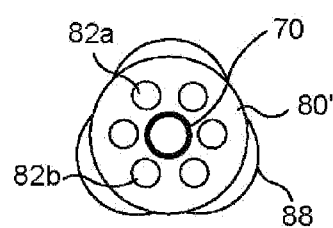

While not required on the flexible endoscope, in many applications, it will be desirable to take a biopsy sample from a nodule or other suspect tissue adjacent to the distal end of the flexible endoscope. While various techniques can be employed to take the biopsy, FIGS. 1F, 1G, and 1H illustrate an exemplary embodiment of a flexible endoscope 24" that includes a rigid portion 26" with a biopsy lumen 117 in which is disposed a flexible shaft 119 having a biopsy needle 121 disposed at its distal end. Also, by detecting light using photodiode sensors at the distal end, as shown in FIGS. 1C and 1D, there is sufficient room proximal to the scanning fiber to encompass both the biopsy channel and tracking sensor 84' within a 2 mm diameter housing. The additional optical sensor wires can be combined with fine tube piezo actuator wires 123. When the flexible endoscope has been positioned and oriented (as determined by the present invention) so that the distal end of the biopsy needle is disposed adjacent to a tissue mass that is to be biopsied, flexible shaft is advanced distally, forcing biopsy needle 121 to extend outwardly of biopsy lumen 117 and into the tissue mass. A plug of the tissue mass remains embedded in the biopsy needle and it can be withdrawn from the site of the biopsy. The specimen retained in the biopsy can then be retrieved when the flexible endoscope is withdrawn from the passages.

Figure 1I:
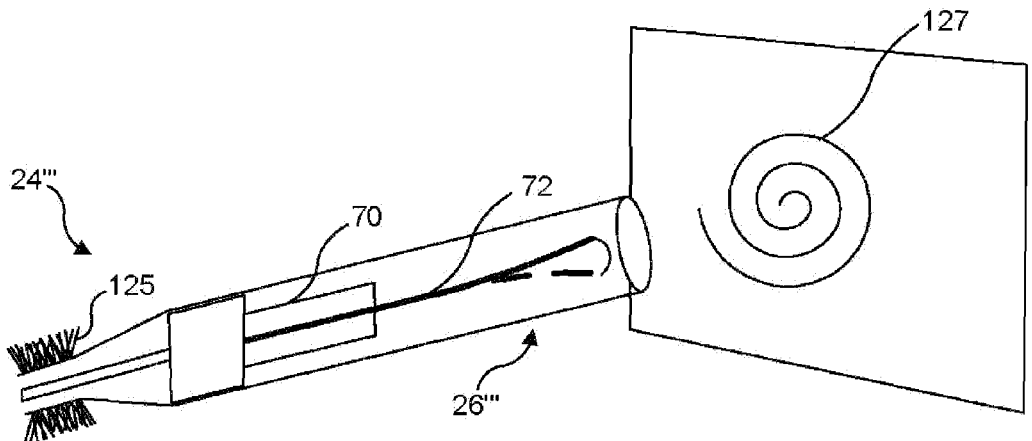

FIG. 1I illustrates a flexible endoscope 24''' in accord with the present invention, that includes a cytological brush 125 for taking tissue samples from the walls of the passage through which the flexible endoscope is advanced. This brush can be advanced over the larger diameter portion of the distal end of the flexible endoscope to take a sample of tissue cells at a desired location using a tubular shaft (not shown) to hold the cannula-style cytological brush. For purposes of simplification, this Figure does not illustrate all of the other components of the flexible endoscope, but it will be understood that either a position sensor or an electromagnetic transmitter will be included in a rigid portion 26''' adjacent to the distal end of the flexible endoscope, generally as described above. In addition, this embodiment will also include either light collecting optical fibers or light detectors to provide an image of the adjacent region. As is true of the other preferred embodiments of the flexible endoscope, in this embodiment, scanning optical fiber 72 is driven so that it scans in a spiral pattern 127.

Model Generation and Registration

While not required, it is preferable, when navigating through a complex set of linked passages in the body, to employ a model of the linked passages so that a route toward a desired point in the body that is in or adjacent to the linked passages. A graphical surface model of the patients bronchial tree can be provided or can be generated from HRCT or MRI scans using a well-known method for segmentation, such as local 3-D region growing or more complex algorithms that incorporate morphological approaches (e.g., as taught by Kiraly et al., in "3-D human airway segmentation for virtual bronchoscopy," *Proc of SPIE* 4683 *Med. Imag.*, 2002). Next, an airway tree model is created from the segmented volume using 3-D skeletonization and branch point detection techniques (e.g., as taught by Kiraly et al., in "Three-dimensional path planning for virtual bronchoscopy," IEEE Trans. Med. Imag., 23(9), 2004). FIG. 3A illustrates a plurality of HRCT scans 162 that have been made of a patient 160 and used to produce a 3-D airway tree model 164. Such techniques have been demonstrated in virtual bronchoscopies. The lateral resolution of HRCT is on the order of 1 mm, (slightly smaller than the smallest airways accessible to the flexible endoscope).

Figure 2C:
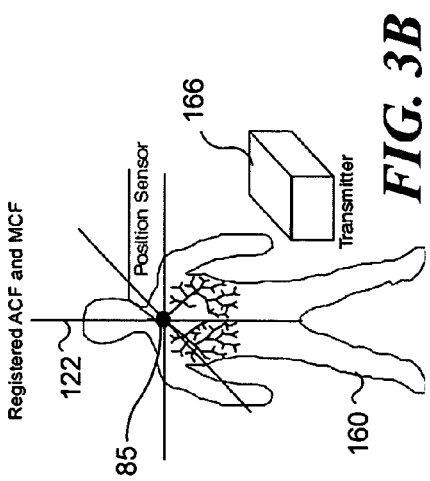
FIG. 2C is a schematic diagram in which a bold arrow points to an inner point of a confluence of two passages into a passage that leads to the main carina.
Figure 2B:
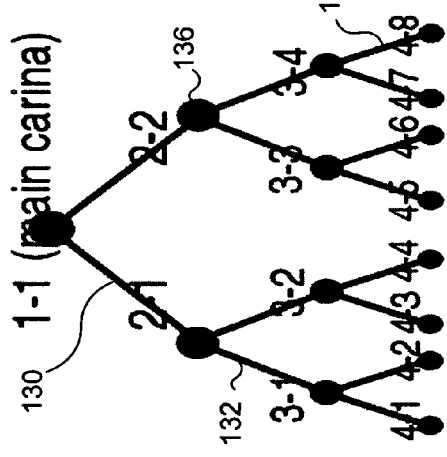
FIG. 2B is an example of a branching node hierarchy specified by i-j, where i is the generation, and j is its index within a model coordinate frame (MCF)
Figure 2A:
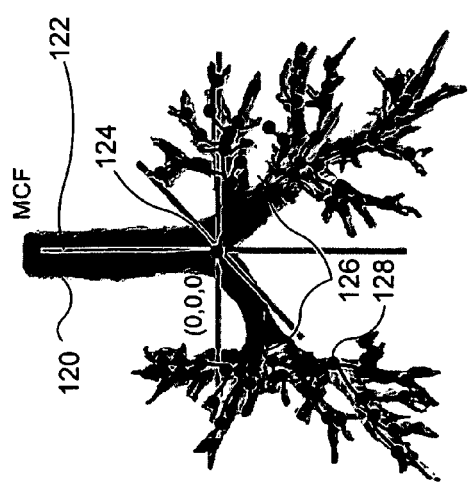
FIG. 2A is a 3-D CT-based surface model and overlying tree model of the bronchial airways, indicating identified nodes and centerlines detected from the skeletonized lung volume, with an origin (0,0,0) set at a main carina.
Figure 2D:
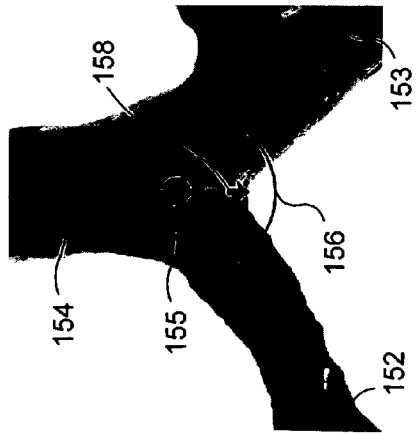

As shown in FIG. 2A, branch points 128 in a model 120 are identified as the intersection of all airways whose position is defined as the inner point of confluence of the two subtending vessels. For example, as shown in FIG. 2C, an airway 140 branches into two airways 142 and 144. An arrow 146 points toward the main carina of the bronchial system, while arrows 148 and 150 point away and down toward two subtending passages 142 and 144, respectively. The bold arrow points to the branch point of these three airways. They can be found automatically by skeletonizing surface model 120 to form a series of centerlines 126 that comprise the airway tree model and selecting all points where these centerlines intersect as branch points 128, as shown in FIG. 2A. A 3-D Cartesian coordinate system 122 is preferably associated with the 3-D model and can have an origin 124 disposed at the first branch point of the bronchial tree, which is the main carina. Because a branch point 155 in the lung tree is found from the intersection of centerlines 154 through skeletonization, this point may not correspond to the actual inner point of confluence, as shown in FIG. 2-D. The appropriate branch point can be defined by projecting a line 158 from this intersection at an angle half that of a branching arc 156 formed by two subtending vessel centerlines 152 and 153, until it intersects with the surface model branch point.

The generation of each node in the skeleton model is determined by counting the number of connections separating it from the main carina. From the example shown in FIG. 2B, it will be evident how a hierarchal tree is computed where every branching node is represented by its generation (e.g., second generation branches 130 that are separated from third generation branches 132 by branch points 136, and so forth, through fourth generation branches 134) and its x-y-z position within the model coordinate frame (MCF). In this example, the MCF is the coordinate system of the lung model. The origin of this coordinate plane may be chosen arbitrarily. For example, the main carina may be chosen as a reference point or origin at coordinates (0,0,0) as shown in FIG. 2A. This coordinate system is otherwise arbitrary and is not affiliated with the position-sensor coordinate system initially.

Once the origin is specified relative to some anatomical feature or other arbitrary point, the MCF is confined to the coordinate space in which the physician maneuvers the device in real-time, otherwise referred to here as the absolute coordinate frame (ACF). While simple point to point alignment does not fully constrain the 3-D lung model in the model coordinate frame (MCF) into the ACF, one or more external position sensor(s) can be affixed to external point(s) on the patient to monitor changes in the orientation of the chest cavity over time due to patient breathing or shifting, as discussed in greater detail below in connection with FIG. 7C.

In one embodiment, the ACF is established by a stationary electromagnetic field transmitter from which the position sensor disposed adjacent to the distal end of the flexible endoscope determines its position and orientation. The system allows for calibration at any arbitrary point 85 in the ACF. When calibrated, this point becomes the origin or reference point of Cartesian coordinate system 122 in the body of patient 160, for both the ACF and MCF, as shown in FIG. 3B. In order to track the sensor position within the MCF, the two must be registered such that a known position in the MCF correlates to a known position in the ACF. A variety of points can be chosen for this purpose, such as the main carina of the patient (as noted above), the collar bone, or any rigid structure identified on the model and accessible to the clinician. It is assumed at this stage that the relative size and shape of the bronchial tree has not changed significantly from the time of the CT scan that was used to produce the 3-D model. A variety of non-rigid registration techniques can also be used by placing additional sensors on the patient and modeling the deformation of the lung due to physiological functions. Because this approach requires registering a discrete number of points in 3-D space, a simpler non-rigid registration method, such as a linear elastic modeling of branch point deformation connected by links would be preferable. However, if the deformation due to tidal breathing can be measured empirically, then the model can be registered from observed data rather than using a heuristic model of airway deformation.

Selecting Points of Biopsy and Course Plotting

Within the MCF, region(s) of interest are selected as intended points of biopsy. Typically, these are nodules or masses found on HRCT scans, and thus have a predefined position in the MCF. The surrounding airways can be elected for interrogation automatically or chosen by the clinician. As shown in FIG. 4A, a series of paths 172 and 174 through bronchial passages 170 are generated based on the branching nodes 176 leading through these airways, for example, to a point of biopsy 178, which is adjacent to a nodule 180. The layout of this course is analogous to a roadmap where navigation relies on a series of decisions or turns one would make in route to reach a desired destination.

Implementation of a Graphical User Interface

Contained within the user interface are windows displaying the 3-D lung surface model and pre-procedural path planning (FIG. 4A), a real-time video image 194 as shown in (FIG. 4B), and a virtual fly-through perspective constructed from the CT scan (FIG. 4C). A graphic marker 192 is displayed in the user interface of FIGURE dB FIG. 4C to show the position of the catheter in airways 190, and the intended navigation routes 204 to the points of biopsy are shown in a static 3-D airway surface model 200 of FIG. 4D along with a current position 202 of the flexible endoscope.

Guided Navigation—Position Calibration

As the scope traverses the airways, the graphical interface is continually updated, charting progress from both global and fly-through perspectives. With reference to FIG. 5A, as the scope approaches a bifurcation 210 in a bronchial passage 212, the user interface indicates which subtending vessel to enter. However, it is necessary to ensure that the scope end is actually at a bifurcation (i.e., that the MCF and ACF are still registered correctly). Before steering the flexible endoscope down either branch, the clinician verifies the position of the flexible endoscope using a touch sensor on the distal end of the flexible endoscope or by visual assessment if necessary. The distal end of the flexible endoscope is touched to the inner point of confluence of the two subtending vessels (i.e., to bifurcation 210) and an input from the clinician on the controller processor initiates a recalibration of the two coordinate frames by registering a position 214 in the MCF of the model to a current actual position 216 in the ACF measured by the position sensor. Model updating can be initiated by the clinician using a foot pedal (not shown) that signals the computer to recalibrate the virtual model by re-registering.

Roadmap Decision Model

Based on the chosen route and the known position and orientation of the catheter tip, a visual graphic is presented on a video monitor to instruct the clinician on how to proceed.

There are three methods described here for assisted navigation at each node in a series of linked bronchial passages: (1) the entire course is plotted within the virtual fly-through and global model perspectives and the clinician must resolve which path to take in the endoscopic imaging window through direct comparison; (2) given the calculated branching angle subtended by the daughter vessels in the airway tree model and as well, the viewing angle of the scanning fiber endoscope, a visual marker is overlaid on top of the endoscopic video images to indicate the intended direction of travel; and (3) image analysis in a bronchial passage 230 is used to segment regions of low intensity by thresholding image and selecting candidate airway regions 238 and 240, which are associated respectively with passages 232 and 234, and a specific path is chosen based on how closely it correlates with the airway tree model structure referenced to Cartesian coordinates 236 (FIG. 5C). Again, as shown in FIG. 5B, a visual marker 222 (e.g., green) is overlaid on top of the scope images, explicitly indicating a correct path choice 220. Here, the deflection angle is represented as a vector of two elements where there is a component of deflection in both the x and y axis of the 2-D endoscopic image. An additional indicator 224 (e.g., red) is also used to signal that a particular region has already been inspected.

Shortest Path Navigation

In many cases, the desired biopsy point lies beyond the airway tree model. It is difficult to segment small airspaces on HRCT and MRI scans and often the reconstructed model is missing branches of the bronchial tree resulting in an unresolved termination of several vessels. However, with reference to an exemplary illustration 250 shown in FIG. 5D, another navigation method can be used, with a dual purpose of navigating the physician to the correct location adjacent nodule 180, as well as extending a model 252 by "growing" the airways, as the flexible endoscope is advanced beyond the model bounds. This technique, as opposed to a roadmap method, operates by minimizing the distance between the present position and the intended destination at every step along the way. This straight shot approach makes the assumption that the seemingly more direct route is the correct route. Obviously, this is not necessarily true and some intervention must be made to correct for wrong decisions. As the remaining airways are traversed, some threshold will be used to signal that the chosen course has deviated too far from the chosen point of biopsy. A record of trial and error navigation is constructed that keeps track of what vessels did not lead to the intended destination. In essence, this decision model operates similarly to a "hot and cold" scenario where a predefined threshold for "cold" governs how far the scope is allowed to veer from the known position of the mass as a direct Euclidean distance, i.e., by setting a limit for the amount of deviation from the desired location toward which the flexible endoscope is being advanced before the current path must be reversed to at least a last branch point. This embodiment of the navigation technique may be used exclusively and may be more practical in other applications where there is little branching.

Model Extension

When the physician approaches a branch point that is beyond the limit of the model, rather than re-registering, the airway tree model can be extended at desired points to establish decision points along the way, while navigating to the point of biopsy. FIG. 5D illustrates how the navigation history is updated and added to airway tree model 254, extending from the open termination of the model of the airways. The model is extended by using the flexible endoscope itself as a tool for mapping rather than from segmented images. Under this scenario, the clinician prompts the computer using some mechanism (e.g., a control button, a foot pedal (neither shown), or a voice command) to record position and orientation measurements and add them to the airway tree model, along with archiving the endoscopic image to the library of images associated with that specific location in the airway tree model. Similarly, erroneous paths or travel markers can be deleted if too susceptible to measurement error.

It is also possible to gate the position measurement at an inspiration level that is the same as that when the CT or MRI scan was taken. This step is achieved by placing one or more external sensors such as position sensor(s), impedance electrode(s), or strain gauge(s) on the sternum, or other such sensor on the thorax, as shown in FIG. 7C, which will then serve as a surrogate for measuring lung volume and thus, lung deformation. This step is done under the assumption that the lung deformation is directly correlated with respiration. Similarly, if using a dynamic lung model in which the deformation of branch points are directly measured, several position readings should be taken in order to accurately predict deformation for dynamic non-rigid registration.

Navigation History

When obtaining tissue specimens from a plurality of locations throughout the lung, it becomes necessary to track the catheter in order to determine a travel history that is displayed on the lung model tree. By doing this, it is possible for the clinician to keep track of lobes that have been explored as well as to revisit a certain region during a follow-up examination. This tool greatly assists the doctor in assuring that all accessible lung regions adjacent to an identified mass have been explored. Additionally, the time expense associated with a physicians need to continually re-orient the catheter to some known position will be greatly diminished while relieving them of the burden of mentally memorizing all explored and unexplored lung regions. This procedure can be done easily by "tagging" branches that have been inspected on the graphical interface; FIG. 5B illustrates a color-coding scheme for labeling explored and unexplored regions. A comparison can be made with a prior evaluation by loading results of the biopsy pertinent to the specific area.

Imaging Techniques for Motion Detection

Despite a physician's best efforts to correctly recalibrate the system to accurately define the tip position within the MCF, a large amount of error impedes the ability to navigate past a certain point, especially when beyond the limits of the 3-D model. In this respect, a subsystem is described for precise navigation along many of the more tightly branching bronchioles of the peripheral lung. Image analysis of subsequent frames obtained from video can be used to analyze movement. A difference image is defined as the subtraction of two images and can be used to detect movement when a given region demonstrates a high degree of change in the pixel values above what is typically observed from noise. In this scenario, difference images are used to discriminate motion induced by noise, error, or breathing (no appearance of motion from the scope's perspective) versus motion resulting from actual extension of the catheter along the vessel path. Once the scope is moved, the position tracking initiates again and does not stop until motion has desisted, as determined from the difference images obtained from the video.

Tracking Position/Orientation of Flexible Endoscope

In an embodiment 270 shown in FIG. 7A, the actual position and orientation of the distal end of the flexible endoscope is tracked using an external electromagnetic field transmitter 276 to produce an electromagnetic field to which a sensor 278 responds by producing corresponding signals indicative of the position and orientation of the distal end of the flexible endoscope. These signals, which are conveyed along with light signals through a lead 280 that is coupled to the proximal end of the flexible endoscope, are processed by external components (i.e., components in a box 282). The flexible endoscope is inserted into the bronchial passages of a patient 272, who is reclining on a non-ferrous bed 274. The electromagnetic field readily penetrates the body of the patient, enabling the realtime tracking of the flexible endoscope in the ACF as the flexible endoscope is advanced through the passages in the bronchial system.

In an alternative embodiment 270' shown in FIG. 7B, an internal electromagnetic field transmitter 290 can be affixed adjacent to the distal end of the flexible endoscope, and one or more external sensors 292 can be employed to respond to the electromagnetic field produced by the internal electromagnetic transmitter, providing corresponding signals that are processed by light source and processor 282 to again determine the position and orientation of the distal end of the flexible endoscope. It is also contemplated that other forms of transmitters and sensors might instead be employed to monitor the position and orientation of the distal end of the flexible endoscope. For example, an external transmitter emitting modulated infrared (IR) light might be employed with a corresponding IR sensor that responds to the IR light received as the light passes through the body of the patient.

Details of an exemplary dipole electromagnetic field transmitter 400 and a corresponding sensor 402 are illustrated in FIG. 9A. As shown in this Figure, electromagnetic field transmitter 400 includes three orthogonally disposed coils 404a, 404b, and 404c, while sensor 402 includes three orthogonal coils 406a, 406b, and 406c. While neither the coils in the transmitter nor the coils in the sensor must be orthogonal to each other, it is preferable that they be so, since the processing of the signals produced by the coils in the sensor is thereby simplified, and the results are likely to be more accurate. As noted above, the electromagnetic field transmitter may be either external to the patient's body or internal, with the sensor being correspondingly internal or external to the patient's body. Appropriate sizing of the transmitter or the sensor is required to enable that component to be fitted adjacent to the distal end of the flexible endoscope.

An alternative configuration of a sensor 402' that includes only two coils 406a and 406b is illustrated in FIG. 9B. If only five degrees of freedom (DOF) are required, then a sensor 402" having only one coil 406b can be employed, as shown in FIG. 9C. It may be preferable to include more coils in either the transmitter and/or receiver than required, since the redundant coil(s) ensure(s) that the position and orientation of the distal end of the flexible endoscope is accurately determined. The product of the number of coils on the sensor and the number of coils on the transmitter must at least equal the number of DOF to be monitored, with the caveat that at least two coils are required on the sensor to sense six DOF. With the ability to determine only five DOF in the embodiment of FIG. 9C, the rotational orientation of the sensor (and the flexible endoscope) will typically be excluded from the determination; however, rotational orientation may not be important in some applications of the flexible endoscope.

Use of Bodily Function Sensor to Minimize Error in Tracking

An embodiment 270''' of FIG. 7C includes an optional band 294 fastened around the thorax of patient 272, to mount a bodily function sensor 296, which responds to the movement of the patient's chest during breathing, to produce a corresponding signal indicative of this bodily function that is conveyed through a cable 298 to light source and processor 282. This signal can be used to synchronize measurements of the position of the distal end of the flexible endoscope with the inhalation/exhalation cycle of the patient, to minimize errors caused by the displacement of the flexible endoscope within the bronchial passages as a result of respiration and movement of the bronchial passages with respiration, or to match the respiration levels of the patient to those at the time the CT or MRI scans were made. FIG. 6 shows how the position of the flexible endoscope can be corrected for the effects of breathing. However, it may be preferable to only take measurements of the position of the flexible endoscope when the patient's breathing cycles are not moving air through the bronchial passages, i.e., at a held-lung volume. The signal produced by sensor 296 enables this option to be readily effected.

An embodiment 270''' as shown in FIG. 7D illustrates yet another approach in which an imaging device 299, such as a laser scanner or a video camera, is employed to scan a pattern of reflective dots 301 that is applied to the thorax of the patient. The imaging of these dots in realtime can produce a graphics signal that indicates the movement of the chest, either due to patient motion or as a result of breathing. The number of sensors used depends on the number of measurements required to determine lung deformation given an a priori model of the bronchial tree dynamics or an empirical model linking bronchial tree deformation with lung volume.

As shown in an embodiment 270''' in FIG. 7E, it is also contemplated that one or more other sensors 303 comprising, for example, position sensors, impedance electrodes, or strain gauges, can be affixed to the thorax of the patient to produce signals directly indicative of lung volume or deformation of the bronchial passages. The one or more motion sensors are coupled to a movement interface 305, which preprocesses the movement signals and supplies a processed movement signal via a cable 307 to the processor in light source and processor 282. Alternatively, it may be preferable to employ a signal produced by one or more sensors that is a surrogate for determining the movement of the bronchial passages. For example, if the external signal is monitored while the flexible endoscope is at a known position, any change in the position of the flexible endoscope during breathing or movement of the chest can be empirically related to the external signal produced by the one or more sensors. Thereafter, the external signal from the one or more sensors can be used indirectly to determine the movement or deformation of the bronchial passages. A dynamic model that accounts for tidal breathing may be obtained from CT scans at multiple levels of inspiration, from position sensing at each bifurcation during the bronchoscopy, or from position sensing performed during a previous bronchoscopy.

Logical Steps Employed in Tracking Flexible Endoscope

FIG. 8A illustrates a flow chart 300 showing the logical steps that are carried out in the present invention. These steps include carrying out a CT scan (or other imaging modality) in a step 302, performing a volumetric segmentation of the bronchial tree, as indicated in a step 304. In addition, the imaging of the lung can be employed to identify any nodules or other regions of interest, where a diagnostic procedure such as a biopsy is to be performed, as indicated in a step 306. In a step 308, the clinician conducts pre-procedural planning, e.g., to determine the steps that should be taken to reach a desired region and carry out the diagnostic procedure, the type of biopsy that will be taken, and other such details. A computer is used to implement skeletonization and branch point detection of the segmented image data, in a step 310, producing results such as shown in FIG. 2B. In a step 312, a six or five DOF tracker is readied to enable the flexible endoscope position and orientation to be tracked as the distal end of the flexible endoscope is advanced through the bronchial passages.

The flexible endoscope will produce a plurality of endoscopic images 313 as it is advanced through the bronchial passages. An array of such images 315 that include overlapping portions can be employed to produce one or more stitched images 342 that are texture-mapped to the surface model. Adjacent images are combined by subtracting one image (pixel-by-pixel) from another image and iteratively moving one image in space to determine the optimal region of overlap, which corresponds to the areas where the error between the two images is minimized. This technique is well-known in the digital image art, and many digital cameras that are currently sold include software for producing a panoramic image (which is completely analogous to the stitched image) from two or more adjacent images. Alternatively, rather than subtracting complete images, matching regions of interest can be identified in both images using a fast search algorithm and then computing multiple motion vectors that provide a good estimation of the total displacement.

Within a virtual interface provided by the model, a step 314, provides for making an initial registration between the MCF and the ACF, as discussed above. This step ensures that some designated point (such as the carina) that is apparent in the model frame of reference is initially set to correspond to the actual location of the flexible endoscope determined by the tracking system. As discussed above, three different approaches can be employed for adaptively updating and re-registering the MCF to the ACF to reach the nodule(s) or other region(s) of interest. These methods include the shortest (or most direct) path approach in a step 316 that is used when moving beyond the extents of the 3-D model, to produce a model extension 328. Within the model, an adapted rigid registration approach can be used, as indicated in a step 318, or an adaptive non-rigid registration approach, as indicated in a step 320. These two approaches can employ automatic calibration using image-based tip tracking (at bifurcations of the passage) at a step 322, manual calibration at automatically selected points in a step 324, or manual calibration at arbitrarily selected points in a step 326, to register the MCF and ACF. At each of these branch points, endoscopic images 313 can be stored in an array of endoscopic images 315 for annotation or later inspection and saved in a library of images 336 within the lung model, for texture mapping 343 and image stitching 342.

Within the ACF, in a step 330, the registration can be carried out in a single measurement at a respiratory-gated level (e.g., determined by one of the bodily function sensors described above), or in a step 332, as multiple measurements of position over the respiratory cycle. The result of either of these two steps is a back registration to the MCF, as indicated in a step 334 for the purpose of establishing a navigation history and charting the clinician's progress in moving the flexible endoscope through an annotated airway tree model.

One goal of the present invention when used in bronchial passages is to provide an annotated lung tree to provide a data record of each of the bronchial passages that was traversed both in regard to the 3-D model, and in regard to mapping the passages and the actual position and orientation of the distal end of the flexible endoscope as it was advanced through these passages. This record will also include endoscopic image library 336 of selected images produced by the scanning optical fiber as it passes through the bronchial passages. The initial 3-D model corresponds to a static airway tree model 338 that is used to display position, record and present findings, and fuse 2-D endoscopic images to a 3-D surface. This model is the basis for a dynamic airway tree model 340 that is more accurate and compensates for the effects of bodily functions, such as breathing. The images produced by the scanning optical fiber in the flexible endoscope correspond to a surface model in which stitched images 342 are texture-mapped to the inside surface. For purposes of possibly revisiting points in a later follow-up procedure and confirming where tissue samples were taken, the surface model will also include a map of all biopsy points 344. Also important are the data comprising a navigation history 346 that indicates each passage through which the flexible endoscope passed during the procedure, as well as other data of interest.

FIG. 8B includes a diagram 331 illustrating the alternative steps for optimized in vivo data analysis that can be employed when updating the 3-D model in the MCF, in a step 353, using the position and orientation measurements made in the ACF (as noted in a block 333). In a step 348, time-averaging of the position measurement may help reduce error in the position measurement as it relates to either re-registering the model or extending the model. A step 350 indicates that the position data for the distal end of the flexible endoscope can be more closely related to the MCF by snapping the position measured to the centerline of the passage in the 3-D model for both real-time virtual image display as well as for precisely determining navigation history relative to the centerlines that comprise the airway tree model. A step 352 may also be implemented to limit position measurement error due to breathing, by only tracking the motion of the endoscope along its axial direction. This movement may be determined as the dot product of the calculated motion vector extending between two points and the forward vector defined by the direction in which the distal tip is pointing. The image shown in FIG. 6 illustrates the view of a small bronchial 161 at inhalation and exhalation. The overall motion of the catheter is measured as the component of an overall motion vector 163 along a forward vector 165 to obtain an error-corrected motion vector 166.

Details of step 316 for determining the shortest or most direct path when navigating beyond the limits of the 3-D model are shown in FIG. 8C. As part of the model extension, it may be necessary to make several position measurements over time to generate either a probabilistic model indicating where small bifurcations are located, or to assist in developing a empirical model for airway deformation as a function of respiration. At a bifurcation, in a step 354, a clinician selectively determines the position and orientation of the distal end of the flexible endoscope based upon the sensor readings. If registration gated position sensing is used, a single measurement of position and orientation is taken in a step 356. If dynamic position sensing is being used, a step 358 provides for taking multiple measurements over an entire respiration cycle. Based on the single or the multiple measurements, in a step 360, the coordinates in the ACF are back-registered to the MCF (i.e., to the last position in the model). A step 362 then provides for adding the new coordinates to the lung tree, so that the model is extended to the current position. It is preferable, that from the current position, a step 364 will then provide an arrow on the virtual interface that indicates a direct path and the distance to the intended destination. While not shown here, if the distance from the intended destination should continue to increase beyond an accepted limit, the clinician may be directed to back up to a previous one or more bifurcation and take a different path.

In FIG. 8D, details of step 322, which provides for automatic calibration using image tracking are shown. A step 366 provides for registering the MCF with the ACF at the current position and orientation of the distal end of the flexible endoscope. Three events can be used to initiate the automatic calibration or registration. In a step 368, the registration procedure is initiated when motion of the distal end of the flexible endoscope is detected by the sensor. In a step 369, motion is detected when the difference image computed by subtracting an acquired endoscopic image and the endoscopic image stored during the last reregistration exceed some threshold. Alternatively, in a step 370, the clinician or other user may initiate the registration by some input. A step 372 indicates that an initial estimate of the new position and orientation is determined based upon the change in position and orientation of the sensor from the previous position and orientation measured during the previous reregistration. During a baseline bronchoscopy, a step 376 generates a surface rendered virtual image from the 3-D model data. Next, using the actual image data produced by the scanning optical fiber, a step 378 computes a similarity between the rendered virtual image and the endoscopic image. As an alternative option, during a follow-up bronchoscopy, a step 374 computes the similarity between the present endoscopic image and a library of endoscopic images acquired during the baseline bronchoscopy with a known position in the MCF. A step 380 then iteratively increments or decrements the position and orientation parameters independently in the MCF, thereby generating a new hi-lighted surface model image or new perspective image of the texture-mapped surface model and computing a new image similarity. If the image similarity has increased, the process repeats by looping back to step 376. However, if the image similarity has not decreased, a step 382 re-registers the MCF to the ACF at the local maximum (i.e., maximum similarity).

There are several ways to determine similarity. Information for the virtual image is not in the structure of the 3-D model, but is based on a projection of the surface rendered model to a two-dimensional (2-D) image, which is done by assuming a point source of white light at the distal end of the flexible endoscope. The virtual model is then rendered as a lighted surface at an appropriate intensity, cone angle, and attenuation factor. These parameters are manipulated to yield the best result (the result that best mimics actual tissue and the flexible endoscope design). Color is not important; the process involves comparing image brightness between endoscopic and virtual images (as taught by Mori et al. in "A method for tracking camera motion of real endoscope by using virtual endoscopy system," Proc. of SPIE 3978, Med. Imag., 2000). Image similarity is then computed as follows. An image error E is calculated by determining the means squared error (MSE) of the two images and dividing by the correlation (Corr) of the images:

$$E=MSE(I_{virtual}, I_{endoscopic})/Corr(I_{virtual}, I_{endoscopic})$$

Minimizing E will produce the most similar match between images.

FIG. 8E includes details of step 320 for adaptive non-rigid registration, for both manual calibration, and for automatic calibration. Under manual calibration, a step 384 determines the ACF position of the distal end of the flexible endoscope, while under the automatic calibration, a step 386 provides that the MCF is automatically re-registered to the ACF by image-based tip tracking at bifurcations in the passage. Two alternatives can then be followed for either manual or automatic at this point. If an a priori model of the bronchial tree or passage deformation based on measuring the position of an external sensor is employed, a step 388 measures the position of the flexible endoscope using multiple sensors or using a plurality of markers that have been placed on the thorax of the patient (as discussed above in connection with FIGS. 7D and 7E). If an empirical model of the bronchial tree deformation is used instead, a step 390 provides for measuring or estimating lung volume (which is only a surrogate for measuring deformation of the bronchial passages). Lung deformation can be found empirically either by taking multiple CT scans at different breath levels, measuring the change in position of the flexible endoscope at each bifurcation using the position sensor, or by using another heuristic model that links respiration level and airway distension. The measurement of respiration level can be taken from the one or more sensors placed on the chest, as in FIG. 7C. p After either step 388 or step 390, a step 392 non-rigidly registers the MCF to the ACF. A step 394 hi-lights a bronchial passageway that leads to an intended destination, on the virtual image provided on the display, so that the clinician knows which branch to follow when advancing the flexible endoscope.

In FIG. 8F, details of step 318 for adaptive rigid registration are illustrated. Again, the registration can be done manually, or automatically. Under manual registration, two approaches can be used. In a step 395, the ACF position is measured using the sensor disposed adjacent to the distal end of the flexible endoscope. In connection with this step, in a step 396, the position is measured using a plurality of sensors that are externally placed on the patient's thorax (i.e., as shown in FIG. 7E). After step 396, a step 397 provides that the MCF is rigidly registered to the ACF.

If automatic registration is used, a step 398 provides that the MCF is automatically re-registered to the ACF by using image-based tip tracking at a bifurcation of the passage. After either step 397 or step 398, a step 399 provides that the bronchial passageway leading to the intended destination is hi-lighted on the virtual image so that the clinician can know the appropriate branch to follow.

Other Considerations

This invention embodies any means of navigating a branching system in vivo including the cardiovascular system, lymphatic system, nasal passages, secretory glands and organs, urethra, pancreas and kidney. Considerations to the proposed methodology may include: (1) other forms of obtaining 3-D models such as using MRI or multimode images such as PET (would it be useful for delivering nuclear contrast agents directly to the lung mass?) and CT (2) determination of catheter position using fluoroscopy or other means of external tracking; and (3) path finding based on other deterministic parameters such as deflection angle and insertion length. Another metric for determining position relies on measurements of the vessel diameter made by side viewing embodiments of the proposed flexible endoscope, such as shown in FIG. 1E, or by using an ultrasound transducer (not shown) mounted at the distal end of the flexible endoscope.

Alterations to the currently proposed method might utilize side-views from a flexible endoscope to locate branch points. Additionally, other visual cues may be applied to this methodology that do not include branch points. In navigation through other branching systems, identification of organs, known abnormalities such as tumors or lesions, or fiducial markers including biocompatible dyes. Discriminating position may also be accomplished by correlating current images obtained from video frames with images already obtained during the procedure using auto-correlation.

In addition to the number of error correction strategies mentioned here, it is also possible to model the lung as a deformable structure and determine probabilistic position of the scope based on established measures of position error obtained from experimentation. Luckily, the flexible endoscope serves as an ideal tool for measuring the extent of deformation or inflation of the lung tissue. Similarly, the lung will deform due to shear stress applied by the flexible endoscope itself particularly within the smaller vessels. Prior knowledge of the tissue characteristics within both the central and peripheral lung help to estimate error in the position measurement. Given this, a form of haptic feedback might be desirable to measure direct forces imposed on the lung by the bronchoscope. In the event that too many errors have accumulated a complete reinsertion and calibration of the ACF and MCF may be desirable.

With regard to the user-interface itself, the 3-D model should be able to be rotated in all directions. Annotations could be logged in a textual or audible form for comparison at a later date. Regions that could not be accessed in previous examinations would have some visual indicator that links to a set of comments or notes made by the same or different physician at an earlier date. Controls to the user-interface could potentially be run by voice command given the preoccupation of the doctor with the manipulation of the bronchoscope. Also, 3-D model viewing could be improved by using an autostereoscopic display or stereoscopic head-mounted display.

Detailed description of the exact route used for navigating to multiple biopsy sites could be integrated into robotic surgery applications so that bronchoscopies could be performed from a remote location while continuing to monitor patient health real-time.

While ultrasound is not commonly used for imaging of the lung due to the high impedance of air, measurements made at the periphery may provide reasonable estimates of the scopes position in vivo.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for visually guiding a flexible endoscope through linked passages within a body, comprising:
    (a) a signal source that emits a reference signal useful for spatially tracking a progress of the flexible endoscope through the linked passages, as the flexible endoscope is flexibly bent around corners while being advanced through the linked passages;
    (b) a sensor that produces an output signal indicating coordinates that define a three-dimensional disposition of a distal end of the flexible endoscope using the reference signal of the signal source to continuously determine the three-dimensional disposition of the distal end as it is advanced through the linked passages;
    (c) a three-dimensional model of the linked passages;
    (d) a processor for determining positions of branching points and for providing indicators that indicate positions of branching points on the three-dimensional model at which the linked passages connect or diverge, said processor specifying at least initially, at least one predefined path on the three-dimensional model from a plurality of paths formed by the linked passages connecting or diverging, along which to advance the flexible endoscope through the linked passages; and
    (e) a display for displaying a view from within the linked passages as the flexible endoscope is advanced therethrough, to enable the flexible endoscope to be visually guided and tracked along a path actually followed through the linked passages, the output signal providing a record of the path followed as the flexible endoscope is advanced and enabling the display to show a current position of the endoscope, relative to the three-dimensional model of the linked passages.

2. The system of claim 1, wherein said three-dimensional model is derived from the record of the sensor output signal acquired during a previous exploration of at least a part of the linked passages.

3. The system of claim 1, wherein the three-dimensional model is derived from an image of a portion of a body in which the linked passages are disposed, the model providing an indication of an orientation and a disposition of the linked passages relative to a specific anatomical feature.

4. The system of claim 1, wherein the signal source comprises an electromagnetic field source, and wherein the signal source and sensor together comprise at least five coils configured to sense at least a three-dimensional position of a distal portion of the flexible endoscope relative to the electromagnetic field source.

5. The system of claim 1, wherein the signal source comprises an electromagnetic field source comprising three coils, and wherein the sensor comprises at least one coil configured to sense at least five degrees of freedom in regard to a three-dimensional position and an orientation of the distal portion of the flexible endoscope.

6. The system of claim 2, further comprising a body function sensor configured to be disposed adjacent to one of a sternum, a thorax, and a mouth of a patient, to monitor at least one of breathing, a chest orientation, and a deformation of airways of a patient, for at least one of updating the three-dimensional model in regard to changes caused by at least one body function, and gating a determination of a disposition of the distal end of the flexible endoscope in regard to the at least one body function.

7. The system of claim 1, wherein the flexible endoscope includes a vibrating optical fiber that scans a region adjacent to the distal end of the flexible endoscope, producing a signal that is used to drive the display.

8. A method for guiding a flexible endoscope through linked passages to either perform a diagnostic procedure or reach a desired location in a patient's body, while tracking the disposition of a distal end of the flexible endoscope, comprising the steps of:
    (a) creating a three-dimensional model of the linked passages;
    (b) specifying positions of branching points at which the linked passages connect or diverge on the three-dimensional model and specifying at least one predefined path from a plurality of paths formed by the linked passages connecting or diverging on the three-dimensional model, along which to advance the flexible endoscope through the linked passages;
    (c) providing an external tracking signal that serves as a reference relative to the linked passages within the patient's body;
    (d) tracking a disposition of the distal end of the flexible endoscope as it is flexibly bent around turns while being advanced along the predefined path through the linked passages, using an output signal produced in response to sensing the external tracking signal, said output signal being produced adjacent to the distal end of the flexible endoscope, the output signal indicating coordinates that define a disposition of the distal end of the flexible endoscope relative to the three-dimensional model as the flexible endoscope is advanced; and
    (e) advancing the distal end of the flexible endoscope around bends through the linked passages along a path corresponding to the predefined path, as determined at least in part by the image of the region and the output signal, to reach the desired location in the patient's body, while resolving any differences between:
        (i) a current position of the distal end of the flexible endoscope within the linked passages, as determined by the sensor output signal; and
        (ii) details of the linked passages as specified by the three-dimensional model.

9. The method of claim 8, wherein the step of providing the external tracking signal comprises the step of transmitting an electromagnetic signal that penetrates the patient's body, the electromagnetic signal providing a three-dimensional reference for determining the position of the distal end of the flexible endoscope relative to the linked passages, as indicated by the output signal.

10. The method of claim 9, wherein the step of tracking further comprises the step of determining a position of the distal end of the flexible endoscope relative to the linked passages using the three-dimensional reference provided by the electromagnetic signal.

11. The method of claim 8, wherein the step of resolving any differences further comprises the steps of using the flexible endoscope for imaging a region of the linked passages that is adjacent to the distal end of the flexible endoscope, and comparing the imaging of the region with the three-dimensional model, to refine and correct an apparent error in the three-dimensional model.

12. The method of claim 11, further comprising the steps of:
    (a) retracting the flexible endoscope away from a region of interest, through the linked passages;
    (b) refining the three-dimensional model based upon the path followed to reach the region of interest; and (c) assigning the path followed to reach the region of interest to a specific passage within the three-dimensional model.

13. The method of claim 11, wherein after the flexible endoscope has been withdrawn from the patient's body, further comprising the step of adjusting the three-dimensional model to match a path followed through the linked passages in reaching at least one region of interest in the patient's body.

14. The method of claim 11, further comprising the steps of:
   (a) monitoring at least one body function that causes changes in a disposition of the linked passages; and
   (b) adjusting the three-dimensional model in regard to data monitored for the at least one body function.

15. The method of claim 14, wherein the step of tracking the disposition of the distal end of the flexible endoscope as it is advanced through the linked passages comprises the step of only enabling tracking function when a state of the at least one body function is substantially identical to that when the three-dimensional model was produced, to minimize an error in tracking the distal end of the flexible endoscope that would otherwise arise due to differences in the state of the at least one body function.

16. The method of claim 8, further comprising the step of using the flexible endoscope for imaging a region of the linked passages that is adjacent to the distal end of the flexible endoscope, to display an image of the region.

17. The method of claim 11, further comprising the step of enabling a user to selectively rotate the three-dimensional model and images produced by imaging with the flexible endoscope.

18. The method of claim 11, wherein the step of advancing comprises the steps of:
   (a) establishing an arbitrary reference point relative to the three-dimensional model for use in determining the path through the linked passages;
   (b) with regard to the arbitrary reference point, establishing three-dimensional model frame coordinates for bifurcations in the linked passages and the desired location; and
   (c) determining at least a portion of the path through the linked passages to the desired location, by reference to the three-dimensional model frame coordinates and by visually detecting each bifurcation as the distal end of the flexible endoscope is advanced through the linked passages.

19. The method of claim 18, wherein the step of advancing further comprises the step of establishing at least one calibration point relative to the three-dimensional model based on an anatomical feature within the patient's body.

20. The method of claim 19, further comprising the step of scanning the anatomical feature with the flexible endoscope.

21. The method of claim 19, further comprising the step of contacting the anatomical feature with the flexible endoscope.

22. The method of claim 19, further comprising the step of imaging the anatomical feature with the flexible endoscope.

23. The method of claim 19, further comprising the step of imaging the anatomical feature with a calibrated field, using the flexible endoscope.

24. The method of claim 23, further comprising the steps of:
   (a) imaging another anatomical feature with another calibrated field, using the flexible endoscope; and
   (b) stitching images of the anatomical feature and the other anatomical feature together, using the calibrated fields.

25. The method of claim 23, further comprising the step of painting the optical image onto the three-dimensional model as a texture map.

26. The method of claim 19, providing a calibrated motion correction to the three-dimensional model for motion of the flexible endoscope relative to the three-dimensional model, by producing a time sequence of images of the anatomical feature.

27. The method of claim 18, wherein the step of advancing further comprises the steps of:
   (a) displaying a graphic image of the three-dimensional model; and
   (b) indicating a position of the distal end of the flexible endoscope on the graphic image, where the position is determined from the output signal.

28. The method of claim 27, wherein the step of advancing further comprises the steps of:
   (a) plotting the path of the distal end of the flexible endoscope as a virtual fly-through of the three-dimensional model before advancing the flexible endoscope through the linked passages; and
   (b) resolving a direction to take at any branching point of the linked passages in the graphic image that is displayed in real-time as the flexible endoscope is advanced through the linked passages along the predefined path, using the model and through direct comparison of the path that was plotted with the position of the distal end of the flexible endoscope indicated on the graphic image.

29. The method of claim 27, wherein the step of advancing further comprises the steps of:
   (a) based on the three-dimensional model, determining an angle of deviation of each subtended branch in the linked passages along which the flexible endoscope may be advanced; and
   (b) on the graphic image, overlaying a visual marker on a branch that should be followed for the path to reach the desired position, to indicate an appropriate direction of travel at the branch corresponding to the predefined path.

30. The method of claim 27, wherein the step of advancing further comprises the steps of:
   (a) analyzing the graphic image showing the position of the distal end of the flexible endoscope to segment regions of low intensity associated with passages at a bifurcation, showing two-dimensional deflection angles for each passage; and
   (b) choosing one of the passages through which to advance the flexible endoscope based upon how closely the two-dimensional deflection angles of said one of the passages correlates with a two-dimensional deflection angle of a passage indicated in the three-dimensional model.

31. The method of claim 27, wherein if the path to reach the desired location is beyond a limit of the three-dimensional model, the step of advancing further comprises the steps of:
   (a) using the output signal employed for tracking, while beyond the limit of the three-dimensional model, computing a time-average position of the distal end of the flexible endoscope; and
   (b) updating the three-dimensional model with a branching tree model, produced from the position of the distal end of the flexible endoscope that was computed and extending from the limit of the three-dimensional model showing each bifurcation and the path along which the flexible endoscope was advanced to produce the branching tree model.

32. The method of claim 31, further comprising the steps of:
- (a) analyzing subsequent image frames produced by the flexible endoscope to evaluate movement of one of the flexible endoscope and the body of the patient based upon determining differences in successive images; and
- (b) refining a position of the distal end of the flexible endoscope based upon the evaluation of the movement.

33. The method of claim 32, further comprising the step of comparing image frames of the linked passages currently produced by the flexible endoscope with previous image frames, for determining the path to follow through the linked passages when advancing the distal end of the flexible endoscope.

34. The method of claim 31, wherein the path followed by the distal end of the flexible endoscope in producing the branching tree model seeks to minimize a distance between the position of the distal end and the desired position, and wherein a predefined threshold for a deviation away from the desired position is applied to determine when to backtrack the flexible endoscope within the linked passages and select a different passage along which to advance the flexible endoscope.

35. The method of claim 31, further comprising the step of only following a path if a current position of the distal end of the flexible endoscope is less than a predefined threshold distance from a desired destination, and if the predefined threshold is exceeded, moving back along the path and taking a different path at a previous branch in the linked passages.

36. The method of claim 31, further comprising the step of displaying a vector indication of a current location and a bearing for the distal end of the flexible endoscope, as feedback to a user who is advancing the flexible endoscope through the linked passages.

37. The method of claim 31, further comprising the step of displaying a delta for each of a plurality of coordinates, and a delta for a total distance, between a current location of the distal end of the flexible endoscope and a desired location in the patient's body.

38. The method of claim 27, further comprising the step of painting a surface of the three-dimensional model that is displayed, with an image that includes a texture, only at a location of an anatomical feature in the patient's body.

39. The method of claim 27, further comprising the steps of:
- (a) imaging anatomical features at spaced-apart locations in a patient's body; and
- (b) painting a surface of the three-dimensional model displayed between the anatomical features, using stitched images that are based on images of the anatomical features.

40. The method of claim 27, further comprising the steps of:
- (a) imaging anatomical features in the patient's body using a calibrated imaging field, producing calibrated images; and
- (b) stitching the calibrated images together to carry out at least one of the steps of:
  - (i) offsetting any accumulated error in the three-dimensional model in regard to tracking the distal end of the flexible endoscope; and
  - (ii) more accurately tracking the distal end of the flexible endoscope when beyond a limit of the three-dimensional model.

41. The method of claim 8, wherein the step of creating the three-demensional model comprises the steps of:
- (a) non-invasively imaging the patient'body where the linked passages are disposed; and
- (b) creating the three-dementional model from the image of linked passages within the patientg'body.

42. The method of claim 8, further comprising the step of taking a tissue sample while the flexible endoscope is within the linked passages.

43. The method of claim 8, further comprising the step of storing data relating to a procedure carried out with the flexible endoscope on the patient.

44. The method of claim 43, wherein the data includes at least one of:
- (a) an indication of the path followed by the flexible endoscope, including at least an indication of passages that were entered with the flexible endoscope;
- (b) a location in the patient's body where a tissue sample was taken with the flexible endoscope;
- (c) a comment by a user of the flexible endoscope during the procedure; and
- (d) an image of the location where the tissue sample was taken.

45. The method of claim 8, further comprising the step of correcting a current position of the distal end of the flexible endoscope in the linked passages for a movement caused by a physiological activity of the patient's body that changes a disposition of a passage in which the distal end of the flexible endoscope is present.

46. The method of claim 8, wherein after the desired location is reached, further comprising the step of enabling a user to selectively record a most efficient path followed by the flexible endoscope through the linked passages to reach the desired location.

47. The method of claim 8, wherein the step of tracking the distal end of the flexible endoscope comprises the step of projecting a position of the distal end of the flexible endoscope to a point on a three-dimensional path defined by the three-dimensional model, said point representing a most likely position of the distal end of the flexible endoscope relative to the linked passages of the three-dimensional model.

48. The method of claim 16, wherein the step of tracking the distal end of the flexible endoscope comprises the step of further refining a position of the distal end of the flexible endoscope to align features identified in the image of the region with feature locations included in the three-dimensional model of the linked passages.

* * * * *